United States Patent
Schuele et al.

(10) Patent No.: US 12,403,037 B2
(45) Date of Patent: Sep. 2, 2025

(54) SUB-NANOSECOND LASER SURGERY SYSTEM UTILIZING MULTIPLE PULSED LASER BEAMS

(71) Applicant: AMO Development, LLC, Santa Ana, CA (US)

(72) Inventors: Georg Schuele, Portola Valley, CA (US); Dan Andersen, Menlo Park, CA (US); Alexander Vankov, Mountain View, CA (US); Phillip H. Gooding, Mountain View, CA (US)

(73) Assignee: AMO Development, LLC, Irvine, CA (US)

( * ) Notice: Subject to any disclaimer, the term of this patent is extended or adjusted under 35 U.S.C. 154(b) by 665 days.

(21) Appl. No.: 17/444,552

(22) Filed: Aug. 5, 2021

(65) Prior Publication Data
US 2021/0361485 A1 Nov. 25, 2021

Related U.S. Application Data

(63) Continuation of application No. 15/183,658, filed on Jun. 15, 2016, now Pat. No. 11,083,625, which is a
(Continued)

(51) Int. Cl.
*A61F 9/008* (2006.01)
*A61F 2/16* (2006.01)

(52) U.S. Cl.
CPC ............ *A61F 9/00825* (2013.01); *A61F 2/16* (2013.01); *A61F 2009/00851* (2013.01);
(Continued)

(58) Field of Classification Search
CPC .... A61F 2009/00851; A61F 2009/0087; A61F 2009/00872; A61F 2009/00887;
(Continued)

(56) References Cited

U.S. PATENT DOCUMENTS

| | | | |
|---|---|---|---|
| 4,538,608 A | | 9/1985 | L'Esperance, Jr. |
| 5,480,396 A | * | 1/1996 | Simon ................. A61F 9/00804 606/4 |

(Continued)

FOREIGN PATENT DOCUMENTS

| | | |
|---|---|---|
| AU | 2008323827 B2 | 11/2013 |
| DE | 19702353 C5 | 3/2004 |

(Continued)

OTHER PUBLICATIONS

Duran S., et al., "Erbium:YAG Laser Emulsification of the Cataractous Lens," Journal of Cataract & Refractive Surgery, 2001, vol. 27 (7), pp. 1025-1032.
(Continued)

*Primary Examiner* — Scott Luan

(57) ABSTRACT

A system for laser ophthalmic surgery includes: a single laser source, under the operative control of a controller, configured to alternatively deliver a first treatment laser beam and a second treatment laser beam. The first treatment laser beam has a pulse energy of 10 to 500 μJ. The second pulsed laser beam has a second pulse energy of about 0.1 to 10 μJ, lower than the first treatment laser beam. An optical system focuses the first treatment laser beam to a first focal spot and directs the first focal spot in a first treatment pattern into a first intraocular target. The optical system also focuses the second treatment laser beam to a second focal spot and direct the second focal spot in a second treatment pattern into a second intraocular target. The first intraocular target and second intraocular target are different.

15 Claims, 9 Drawing Sheets

Related U.S. Application Data continuation-in-part of application No. 14/973,508, filed on Dec. 17, 2015, now Pat. No. 10,485,705.

(60) Provisional application No. 62/187,771, filed on Jul. 1, 2015.

(52) U.S. Cl.
CPC ............... *A61F 2009/0087* (2013.01); *A61F 2009/00872* (2013.01); *A61F 2009/00887* (2013.01); *A61F 2009/00889* (2013.01); *A61F 2009/00897* (2013.01)

(58) Field of Classification Search
CPC .. A61F 2009/00889; A61F 2009/00897; A61F 2/16; A61F 9/00825
See application file for complete search history.

(56) References Cited

U.S. PATENT DOCUMENTS

| | | | |
|---|---|---|---|
| 5,657,138 | A | 8/1997 | Lewis et al. |
| 5,720,894 | A | 2/1998 | Neev et al. |
| 5,957,915 | A | 9/1999 | Trost |
| 5,984,916 | A | 11/1999 | Lai |
| 6,019,472 | A | 2/2000 | Koester et al. |
| 6,391,020 | B1 | 5/2002 | Kurtz et al. |
| 6,454,761 | B1 | 9/2002 | Freedman |
| 7,008,415 | B2 | 3/2006 | Yee et al. |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 8,475,438 | B2 | 7/2013 | Larsen |
| 8,709,001 | B2 | 4/2014 | Blumenkranz et al. |
| 8,758,332 | B2 | 6/2014 | Frey et al. |
| 2002/0013574 | A1 | 1/2002 | Elbrecht et al. |
| 2003/0142703 | A1 | 7/2003 | Gao et al. |
| 2009/0137991 | A1 | 5/2009 | Kurtz |
| 2009/0171327 | A1 | 7/2009 | Kurtz et al. |
| 2009/0177189 | A1 | 7/2009 | Raksi |
| 2010/0191230 | A1 | 7/2010 | Dick et al. |
| 2011/0172649 | A1* | 7/2011 | Schuele ................. A61F 9/008 606/4 |
| 2011/0178512 | A1 | 7/2011 | Blumenkranz et al. |
| 2011/0184395 | A1 | 7/2011 | Schuele et al. |
| 2011/0196350 | A1 | 8/2011 | Friedman et al. |
| 2011/0319873 | A1 | 12/2011 | Raksi et al. |
| 2011/0319875 | A1 | 12/2011 | Loesel et al. |
| 2012/0016350 | A1 | 1/2012 | Myers et al. |
| 2012/0089134 | A1 | 4/2012 | Horvath et al. |
| 2012/0259321 | A1 | 10/2012 | Vera et al. |
| 2012/0296319 | A1 | 11/2012 | Chaudhary et al. |
| 2012/0316544 | A1 | 12/2012 | Horvath et al. |
| 2013/0103013 | A1 | 4/2013 | Esposito |
| 2013/0158530 | A1 | 6/2013 | Goldshleger et al. |
| 2013/0338648 | A1 | 12/2013 | Hanebuchi et al. |
| 2014/0114297 | A1 | 4/2014 | Woodley et al. |
| 2014/0128821 | A1 | 5/2014 | Gooding et al. |
| 2014/0128853 | A1 | 5/2014 | Angeley et al. |
| 2014/0135749 | A1 | 5/2014 | Goh et al. |
| 2014/0163534 | A1 | 6/2014 | Angeley et al. |
| 2014/0194860 | A1 | 7/2014 | Dick et al. |
| 2014/0200563 | A1 | 7/2014 | Fu et al. |
| 2014/0276680 | A1 | 9/2014 | Dennison et al. |
| 2014/0316389 | A1* | 10/2014 | Schuele ............. A61F 9/00825 606/5 |
| 2015/0342678 | A1 | 12/2015 | Deladurantaye et al. |

FOREIGN PATENT DOCUMENTS

| | | |
|---|---|---|
| EP | 2574318 A1 | 4/2013 |
| WO | 9308677 A2 | 5/1993 |
| WO | 2011085274 A1 | 7/2011 |
| WO | 2014032678 A1 | 3/2014 |

OTHER PUBLICATIONS

Mastropasqua L., et al., "Scanning Electron Microscopy Evaluation of Capsulorhexis in Femtosecond Laser-Assisted Cataract Surgery," Journal of Cataract & Refractive Surgery, 2013, vol. 39 (10), pp. 1581-1586.

Palanker D.V., et al., "Femtosecond Laser-Assisted Cataract Surgery with Integrated Optical Coherence Tomography," Science Translational Medicine, 2010, vol. 2 (58), p. 58ra85.

Wetzel W., et al., "Photofragmentation of Lens Nuclei Using the Er:YAG laser: Preliminary Report of an in Vitro Study," German Journal of Ophthalmology, 1996, vol. 5 (5), pp. 281-284.

\* cited by examiner

SUB-NANOSECOND LASER SURGERY SYSTEM UTILIZING MULTIPLE PULSED LASER BEAMS

CROSS-REFERENCE TO RELATED APPLICATIONS

This application is a continuation of, and claims the benefit of priority to U.S. patent application Ser. No. 15/183,658, filed Jun. 15, 2016, which is a continuation-in-part of, and claims the benefit of priority to U.S. patent application Ser. No. 14/973,508, filed Dec. 17, 2015, which is a non-provisional application of and claims the benefit of priority to U.S. Provisional Patent Application Ser. No. 62/187,771, filed Jul. 1, 2015, the entire contents of all of which are incorporated herein by reference in their entirety.

BACKGROUND

The present disclosure relates generally to tissue cutting induced by a pulsed laser beam and the energy of the pulsed laser beam. Although specific reference is made to cutting tissue for surgery such as cataract surgery, embodiments as described herein can be used in many ways with many materials to treat one or more of many materials, such as cutting of optically transparent materials.

Cutting of materials can be done mechanically with chisels, knives, scalpels and other tools such as surgical tools. Pulsed lasers can be used to cut one or more of many materials and have been used for laser surgery to cut tissue. However, prior methods and apparatus of cutting can be less than desirable in at least some instances. For example, at least some prior methods and apparatus for cutting materials such as tissue are unsuitable due to their cost and size.

Cataract extraction is one of the most commonly performed surgical procedures in the world. A cataract is formed by opacification of the crystalline lens or its envelope (the lens capsule) of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule through which the surgeon excises the whole lens. Access to the lens can also be provided by performing a manual continuous curvilinear capsulorhexis (CCC) procedure. The lens may then be fragmented by segmenting and/or softening the lens by a femtosecond laser to aid in removal by a phacoemulsification tip. Removal of the lens with the phacoemulsification tip is then performed through a primary corneal incision, for instance. After removal of the lens nucleus, a synthetic foldable intraocular lens (IOL) can be inserted into the remaining lens capsule of the eye.

Prior methods and apparatuses to incise tissue with laser beams can be less than ideal in at least some instances. For example, femtosecond laser cutting systems are used in performing lens fragmentation. Femtosecond laser technology provides a short duration (e.g., approximately 10-13 seconds in duration) laser pulse (with energy level in the micro joule range) that can be delivered to a tightly focused point to disrupt tissue. Femtosecond lasers are well-suited for providing clean cuts in a lens through a relatively wide range of energy levels. However, the high cost and large size of femtosecond laser cutting systems prevent those systems from more widespread usage.

Infrared laser cutting systems, such as picosecond lasers, are smaller and more cost-effective relative to femtosecond laser cutting systems, but are not used for lens fragmentation. These systems provide cuts to a nucleus of the lens with energy level in the tens of micro joule range that are coarser than the cuts provided by a femtosecond laser beam. The quality of the cuts are poor and non-uniform throughout the lens, resulting in defects such as patching, incomplete cuts and excess damage from large bubbles generated by the laser. Examples of incomplete cutting include bridging where two cut portions remain connected together, thereby complicating subsequent nucleus removal. Excess damage to the tissue creates lamella separation that cracks the lens and block subsequent laser pulses. Therefore, further laser cutting is not possible once a lens is delaminated. Although infrared laser systems are attractive from a cost perspective, these performance deficiencies have prevented their use for lens fragmentation.

Thus, improved methods and systems for lens fragmentation and treating cataracts are needed. In light of the above, it would be desirable to have improved methods and apparatus of treating materials with laser beams, such as the surgical cutting of tissue to treat cataracts with cost effective surgical systems. At least some of the above deficiencies of the prior methods and apparatus are overcome by the embodiments described herein.

SUMMARY

Improved laser eye surgery systems, and related methods, are provided. The laser eye surgery systems provide the capability of performing multiple aspects of laser cataract surgery, including the use a single laser source to form precise incisions in the cornea, lens capsule, crystalline lens nucleus and further to perform lens fragmentation of the crystalline nucleus. Although specific reference is made to tissue cutting for laser eye surgery, embodiments as described herein can be used in one or more of many ways with many surgical procedures and devices, such as orthopedic surgery, robotic surgery and microkeratomes.

In many embodiments, a system for laser ophthalmic surgery on an eye of a patient comprises: a single laser source, under the operative control of a controller, configured to alternatively deliver a first treatment laser beam and a second treatment laser beam, each treatment laser beam comprising a plurality of laser pulses, the first treatment laser beam having a pulse energy of about 10 to 500 μJ and the second pulsed laser beam having a second pulse energy of about 0.1 to 10 μJ and lower than the first treatment laser beam; and an optical system operatively coupled to the laser source by the controller and configured to focus the first treatment laser beam to a first focal spot and direct the first focal spot in a first treatment pattern into one or more intraocular targets, including a first intraocular target. The optical system is further configured to focus the second treatment laser beam to a second focal spot and direct the second focal spot in a second treatment pattern into the one or more intraocular targets, including a second intraocular target. The first intraocular target is different than the second intraocular target.

In many embodiments, a method for laser ophthalmic surgery on an eye of a patient comprises: alternatively delivering, using a single laser source, a first treatment laser beam and a second treatment laser beam, each treatment laser beam comprising a plurality of laser pulses, focusing the first treatment laser beam to a first focal spot and directing the first focal spot in a first treatment pattern into one or more intraocular targets, including a first intraocular target; and focusing the second treatment laser beam to a second focal spot and directing the second focal spot in a second treatment pattern into the one or more intraocular targets, including a second intraocular target. The first treatment laser beam has a pulse energy of about 10 to 500 μJ and the second pulsed laser beam has a second pulse energy of about 0.1 to 10 μJ and is lower than the first treatment laser beam. The first intraocular target is different than the second intraocular target.

In many embodiments, the one or more intraocular targets may be selected from the group consisting of a cornea, a limbus, a sclera, an anterior portion of a lens capsule, a crystalline lens, a posterior portion of the lens capsule, and a synthetic intraocular lens implant.

In many embodiments, a repetition rate of the first treatment laser beam is about 1 to 50 KHz and wherein the second treatment laser beam has a repetition rate of about 50 to 200 KHz and is higher than that of the first treatment laser beam of between.

In many embodiments, a pulse duration of the first treatment laser beams is less than 1 nanosecond, or less than or equal to 500 ps, or less than or equal to 150 ps, and a pulse duration of the second treatment laser beam is less than 1 nanosecond or less than or equal to 500 ps, or less than or equal to 150 ps.

In many embodiments, a pulse duration of the first treatment laser beams is greater than 10 fs, or greater than 500 fs or greater than 999 fs, and a pulse duration of the second treatment laser beam is greater than 10 fs, or greater than 500 fs or greater than 999 fs In many embodiments, a pulse duration of first treatment laser beam is about 1 ps and 150 ps, and a pulse duration of the second treatment laser beam is about 1 ps and 150 ps.

In many embodiments, the laser pulses of first treatment laser beam have a first wavelength and the laser pulses of second treatment laser beam have a second wavelength different from the first wavelength, and each of the first and second wavelengths is independently selected from the group consisting of an infrared wavelength, a visible wavelength pulses and an ultraviolet wavelength.

In many embodiments, the first wavelength is an infrared wavelength, and the infrared wavelength may be 870 nm to 1200 nm. In many embodiments, the second wavelength is an ultraviolet wavelength, and the ultraviolet wavelength may be 320 nm to 370 nm.

In some embodiments, the first treatment laser beam is an infrared wavelength beam with a wavelength between 1050 nm to 1100 nm, a pulse energy of between about 10 and 500 μJ and repetition rate between about 1 and 50 KHz, and the second treatment laser beam is an ultraviolet wavelength beam having a wavelength of 320 nm to 370 nm, a pulse energy of about 0.1 to 10 μJ and repetition rate of 50 to 200 KHz.

In many embodiments, the first intraocular target one or more selected from the group consisting of the crystalline lens and the posterior portion of the lens capsule.

In many embodiments, the first intraocular target is the crystalline lens, and the first treatment pattern is a lens fragmentation treatment pattern.

In many embodiments, the first intraocular target is the posterior portion of the lens capsule, and the first treatment pattern is a posterior capsulotomy treatment pattern.

In many embodiments, the second intraocular target is one or more selected from the group consisting of the cornea and the anterior lens capsule.

In many embodiments, the second intraocular target is the cornea, and the second treatment pattern is selected from the group consisting of an arcuate incision treatment pattern, a primary cataract incision treatment pattern, and a sideport incision treatment pattern.

In many embodiments, the second intraocular target is the anterior lens capsule, and the second treatment pattern is a capsulotomy treatment pattern.

In many embodiments of a system for laser ophthalmic surgery, both treatment patterns are conducted along the same optical path from the light source to the eye in the direction of propagation of the laser beam. Thus, in many embodiments, the optical system comprises an objective lens, and optical system is configured to direct both the first treatment laser beam and the second treatment laser beam along a same optical path from the laser source to the objective lens. In these embodiments, the laser source is configured to alternatively deliver a first probe laser beam corresponding to the first treatment laser beam and a second probe laser beam corresponding to the second treatment laser beam. The first probe laser beam may be obtained, for instance, by attenuating the first treatment beam. The second probe laser beam may be obtained, for instance, by attenuating second treatment beam. An imaging system operatively coupled to the laser source and optical system by the controller is configured to direct the first probe laser beam to the at least one or more intraocular targets and to confocally detect back reflected light of the first probe laser beam from the at least one or more intraocular targets, thereby obtaining first image data corresponding a first area of the one or more intraocular targets. The imaging system being is also configured to direct the second probe laser beam to the at least one or more intraocular targets and to confocally detect back reflected light of the probe laser beam from the at least one or more intraocular targets, thereby obtaining second image data corresponding to a second area of the one or more intraocular targets. The first area is different from the second area.

In many embodiments of a method for ophthalmic surgery, the method further comprises: directing both the first treatment laser beam and the second treatment laser beam along a same optical path from the laser source to the objective lens in a direction of propagation of the first and second laser beams. The method may also comprise: alternatively delivering a first probe laser beam corresponding to the first treatment laser beam and a second probe laser beam corresponding to the second treatment laser beam; directing the first probe laser beam to the at least one or more intraocular targets and confocally detecting back reflected light of the first probe laser beam from the at least one or more intraocular targets, thereby obtaining first image data corresponding a first area of the one or more intraocular targets; and directing the second probe laser beam to the at least one or more intraocular targets and confocally detecting back reflected light of the probe laser beam from the at least one or more intraocular targets, thereby obtaining second image data corresponding to a second area of the one or more intraocular targets. The first area is different from the second area.

In many embodiments, the one or more intraocular targets may be selected from the group consisting of a cornea, a limbus, a sclera, an anterior portion of a lens capsule, a crystalline lens, a posterior portion of the lens capsule, and a synthetic intraocular lens implant.

In many embodiments, the first area comprises one or more portions of ophthalmic tissue selected from the group consisting of the crystalline lens, the posterior portion of the lens capsule, and the posterior pole of the eye. The first treatment pattern is preferably determined based at least in part on the first image data.

In many embodiments, the first area is at least a portion of the crystalline lens, the first image data corresponds to image data of the crystalline lens, the first treatment pattern is a lens fragmentation treatment pattern, and the lens fragmentation treatment pattern is determined based at least in part on the image data of the crystalline lens.

In many embodiments, the second area is one or more portions of ophthalmic tissue selected from the group consisting of the cornea and the anterior lens capsule. The second treatment pattern is preferably determined based at least in part on the second image data.

In many embodiments, the second area is at least a portion of the cornea, the second image data corresponds to image data of the cornea, the second treatment pattern is a cataract incision treatment pattern, and the cataract incision treatment pattern is determined based at least in part on the image data of the cornea.

In many embodiments, the second area is at least a portion of the cornea, the second image data corresponds to image data of the cornea, the second treatment pattern is an arcuate incision treatment pattern, and the arcuate incision treatment pattern is determined based at least in part on the image data of the cornea.

In many embodiments, the second area is at least a portion of the cornea, the second image data corresponds to image data of the cornea, the second treatment pattern is a sideport incision treatment pattern, and the sideport incision treatment pattern is determined based at least in part on the image data of the cornea.

In many embodiments of a system for laser ophthalmic surgery, the first treatment beam and the second treatment beam are delivered along different optical path segments in a direction of propagation of the light beam. in a direction of propagation from the laser source to the objective lens in many embodiments, the optical path is configured to separate the first and second treatment laser beams so as to divert the first treatment laser beam along a first optical path segment, to divert the second treatment laser beam along a different, second optical path segment and to recombine the first and second probe laser beams prior to passing through an objective lens. In many of these embodiments, the laser source is configured to alternatively deliver a first probe laser beam corresponding to the first treatment laser beam and a second probe laser beam corresponding to the second treatment laser beam. The first probe laser beam may be obtained, for instance, by attenuating the first treatment beam. The second probe laser beam may be obtained, for instance, by attenuating second treatment beam. A first imaging system is operatively coupled to the laser source and the optical system by the controller and configured to direct the first probe laser beam to the at least one or more intraocular targets and to confocally detect back reflected light of the first probe laser beam from the at least one or more intraocular targets back directed along the first optical path segment, thereby obtaining first image data corresponding a first area of the one or more intraocular targets. A second imaging system operatively coupled to the laser source and optical system by the controller and configured to direct the second probe laser beam to the at least one or more intraocular targets and to confocally detect back reflected light of the second probe laser beam from the at least one or more intraocular targets along the second optical path segment, thereby obtaining second image data corresponding a second area of the one or more intraocular targets. The first area is different from the second area.

In many embodiments of a method of laser ophthalmic surgery, the method comprises: in a direction of propagation from the laser source to the objective lens, separating the first and second treatment laser beams, thereby diverting the first treatment laser beam along a first optical path segment, diverting the second treatment laser beam along a different, second optical path segment and recombining and directing the first and second probe laser beams along a same optical path prior to passing through an objective lens. The method may further comprise: alternatively delivering a first probe laser beam corresponding to the first treatment laser beam and a second probe laser beam corresponding to the second treatment laser beam; directing the first probe laser beam to the at least one or more intraocular targets and confocally detecting back reflected light of the first probe laser beam from the at least one or more intraocular targets back directed along the first optical path segment, thereby obtaining first image data corresponding a first area of the one or more intraocular targets; and directing the second probe laser beam to the at least one or more intraocular targets and confocally detecting back reflected light of the second probe laser beam from the at least one or more intraocular targets along the second optical path segment, thereby obtaining second image data corresponding a second area of the one or more intraocular targets, The first area is different from the second area.

In many embodiments, the one or more intraocular targets may be selected from the group consisting of a cornea, a limbus, a sclera, an anterior portion of a lens capsule, a crystalline lens, a posterior portion of the lens capsule, and a synthetic intraocular lens implant.

In many embodiments, the first area comprises one or more portions of ophthalmic tissue selected from the group consisting of the crystalline lens, the posterior portion of the lens capsule, and the posterior pole of the eye. The first treatment pattern is determined based at least in part on the first image data.

In many embodiments the first area is at least a portion of the crystalline lens, the first image data corresponds to image data of the crystalline lens, the first treatment pattern is a lens fragmentation pattern, and the lens fragmentation pattern is determined based at least in part on the image data of the crystalline lens.

In many embodiments, the second area is one or more portions of ophthalmic tissue selected from the group consisting of the cornea and the anterior lens capsule. The second treatment pattern is preferably determined based at least in part on the second image data.

In many embodiments, the second area is at least a portion of the cornea, the second image data corresponds to image data of the cornea, the second treatment pattern is a cataract incision, and the cataract incision is determined based at least in part on the image data of the cornea.

In many embodiments, the second area is at least a portion of the cornea, the second image data corresponds to image data of the cornea, the second treatment pattern is an arcuate incision, and the arcuate incision is determined based at least in part on the image data of the cornea.

In many embodiments, the second area is at least a portion of the cornea, the second image data corresponds to image data of the cornea, the second treatment pattern is a sideport incision, and the arcuate incision is determined based at least in part on the image data of the cornea.

An optical delivery system may be coupled to the sub-nanosecond laser source to receive and direct the treatment beam. A processor may be coupled to the sub-nanosecond laser source and the optical delivery system. The processor includes a tangible non-volatile computer readable medium including instructions to determine a lens cut pattern for lens fragmentation and determine a plurality of energies of the treatment beam as a linear function of a depth of the lens cut pattern. The treatment beam may be output according to the lens cut pattern and the determined energies.

In some embodiments, the plurality of energies of the treatment beam may be between twice an energy threshold and ten times an energy threshold. The energy threshold is an energy level at which visible damage in tissue is first observed. In some variations, the sub-nanosecond laser source generates the treatment beam with an energy five times the energy threshold of the tissue. The sub-nanosecond laser source may be a picosecond laser. The sub-nanosecond laser may generate a 150 picosecond treatment beam.

In some embodiments, the laser system may include an image capture system for capturing an image of the eye. A patient interface system may couple the eye with the optical delivery system so as to constrain the eye relative to the optical delivery system. In some embodiments, a method of fragmenting a lens is provided and includes the steps of determining a lens cut pattern for lens fragmentation. A treatment beam may be generated that includes a plurality of laser beam pulses by a sub-nanosecond laser source. A plurality of energies of the treatment beam may be determined as a linear function of a depth of the lens cut pattern. The treatment beam may be output according to the lens cut pattern and the determined energies.

In some embodiments, the plurality of energies of the treatment beam is between twice an energy threshold and ten times an energy threshold. The energy threshold may be an energy level at which visible damage in tissue is first observed. The sub-nanosecond laser source may generate the treatment beam with an energy five times the energy threshold of the tissue. The sub-nanosecond laser source may be a picosecond laser. The sub-nanosecond laser may generate a 150 picosecond treatment beam.

In other embodiments, an image of the eye may be captured by an image capture system. The eye may be coupled with the optical delivery system so as to constrain the eye relative to the optical delivery system by a patient interface system.

Disclosed are systems and methods of laser induced fragmentation of a cataractous lens, generally in connection with laser cataract surgery.

In many embodiments, a method of making an incision in a cataractous lens during a laser cataract surgical procedure comprises: identifying a cutting region in the posterior portion of a cataractous lens, the cutting region being defined by an anterior cutting boundary, a posterior cutting boundary and a lateral cutting boundary, the cutting region including the optical axis of the eye and a peripheral portion of the lens spaced laterally from the optical axis; generating a beam of light using a pulsed laser system guided by a control system so as to scan the beam in a lens fragmentation scanning pattern within the cutting region to segment the crystalline lens into a plurality of segments for subsequent removal, the scanning pattern for the segmentation of the crystalline lens including: focusing the beam at a first focal point located at a first depth in the eye tissue and scanning the beam on the eye while focused at the first depth in a lateral direction from a peripheral portion of the lens toward the optical axis of the eye so as to create an first incision pattern corresponding to a first portion of the lens fragmentation pattern, and focusing the beam at a second focal point at a second depth anterior to the first depth, and scanning the beam on the eye while focused at the second depth so as to create a second incision pattern within the cutting region at the second depth corresponding to second portion of the lens fragmentation pattern.

In many embodiments, the method comprises operating an imaging system so as to acquire image data of a volume of a crystalline lens of a patient and construct one or more images of the patient's eye tissues from the image data, wherein the one or more images include an image of at least a posterior portion of the crystalline lens; and identifying the cutting region based on the image data.

A method of making an incision in a cataractous lens during a cataract surgical procedure comprises: operating an imaging system so as to acquire image data of a volume of a crystalline lens of a patient and construct one or more images of the patient's eye tissues from the image data, wherein the one or more images include an image of at least a posterior portion of the crystalline lens; identifying a cutting region in a posterior portion of the crystalline lens based on the image data, the cutting region being at least partially defined by an anterior cutting boundary, a posterior cutting boundary and a lateral cutting boundary of the crystalline lens, the cutting region including the optical axis of the eye and a peripheral portion of the lens spaced laterally from the optical axis; generating a beam of light using a pulsed laser system guided by the control system so as to scan the beam in a lens fragmentation scanning pattern within the cutting region to segment the crystalline lens into a plurality of pieces for subsequent removal, the lens fragmentation scanning pattern for the segmentation of the crystalline lens including: focusing the beam at a first focal point located at a first depth in the eye tissue and scanning the beam on the eye while focused at the first depth so as to create a first incision pattern corresponding to a first portion of the lens fragmentation pattern, and focusing the beam at a second focal point at a second depth anterior to the first depth, and scanning the beam on the eye while focused at the second depth so as to create a second incision pattern corresponding to a second portion of the lens fragmentation pattern within the cutting region at the second depth, wherein an energy of the laser pulses of the laser pulses incident on the tissue at the second depth increases when focal point is scanned in a direction from the optical axis to the peripheral portion.

The method further comprises operating an imaging system so as to acquire image data of a volume of a crystalline lens of a patient and construct one or more images of the patient's eye tissues from the image data, wherein the one or more images include an image of at least a posterior portion of the crystalline lens; and identifying the cutting region based on the image data.

A laser surgical system for making incisions in a cataractous lens during a cataract surgical procedure comprises a laser system and a control system. The laser system comprises a scanning assembly and a laser operable to generate a laser beam configured to incise the cataractous lens. The control system is operably coupled to the laser system and configured to: determine a lens fragmentation scanning pattern for scanning a focal zone of the laser beam in a cutting region in a posterior portion of the crystalline lens based on the image data, the cutting region being at least partially defined by an anterior cutting boundary, a posterior cutting boundary and a lateral cutting boundary of the crystalline lens, the cutting region including the optical axis of the eye and a peripheral portion of the lens spaced laterally from the optical axis; operate the laser and the scanning assembly to scan the focal zone of the laser beam focusing the beam at a first focal point located at a first depth in the eye tissue and scanning the beam on the eye while focused at the first depth so as to create a first incision pattern corresponding to first portion of the lens fragmentation pattern, and operate the laser and scanning assembly to scan the laser beam at a second focal point at a second depth anterior to the first depth, and to scan the beam on the eye while focused at the second depth so as to create a second incision pattern corresponding to a second portion of the lens fragmentation pattern within the cutting region at the second depth, wherein an energy of the laser pulses scanning the second incision pattern increases when focal point is scanned in a direction from the optical axis to the peripheral portion.

In many embodiments, the system further comprises an imaging device configured to acquire point by point image data from locations distributed throughout a volume of a crystalline lens of the patient and construct one or more images of the patient's eye tissues from the image data, wherein the one or more images comprise an image of at least a portion of the crystalline lens. The control system is further configured to: operate the imaging device to generate image data for patient's crystalline lens; process the image data to identify a location for each of one or more targets in the lens of the patient, the one or more targets within the cutting region.

In another embodiment, a laser surgical system for making incisions in a cataractous lens during a cataract surgical procedure comprises a laser system and a control system. The laser system includes a scanning assembly, and a laser operable to generate a laser beam configured to incise the cataractous lens. The control system operably coupled to the laser system and configured to: determine a lens fragmentation scanning pattern for scanning a focal zone of the laser beam in a cutting region in a posterior portion of the crystalline lens based on the image data, the cutting region being at least partially defined by an anterior cutting boundary, a posterior cutting boundary and a lateral cutting boundary of the crystalline lens, the cutting region including the optical axis of the eye and a peripheral portion of the lens spaced laterally from the optical axis; and operate the laser and the scanning assembly to scan the focal zone of the laser beam focusing the beam at a first focal point located at a first depth in the eye tissue and scanning the beam on the eye while focused at the first depth in a lateral direction from a peripheral portion of the lens toward the optical axis of the eye so as to create a first incision pattern corresponding to first portion of the lens fragmentation pattern; and operate the laser and scanning assembly to scan the laser beam at a second focal point at a second depth anterior to the first depth, and to scan the beam on the eye while focused at the second depth so as to create a second incision pattern corresponding to a second portion of the lens fragmentation pattern within the cutting region at the second depth.

The system preferably comprises an imaging device configured to acquire point by point image data from locations distributed throughout a volume of a crystalline lens of the patient and construct one or more images of the patient's eye tissues from the image data, wherein the one or more images comprise an image of at least a portion of the crystalline lens. The control system is preferably further configured to operate the imaging device to generate image data for patient's crystalline lens and process the image data to identify a location for each of one or more targets in the lens of the patient, the one or more targets within the cutting region.

In many embodiments, the lens fragmentation pattern comprises either two crossing cut incisions, three crossing cut incisions or four crossing cut incisions. In many embodiments, the lens fragmentation pattern comprises two and only two crossing cut incisions, thereby producing 4 quadrants. The lens fragmentation patter further comprises softening cuts in each quadrant.

Various embodiments of the laser eye surgery system are provided. For example, a laser cataract surgery system includes a sub-nanosecond laser source generating a treatment beam that includes a plurality of laser beam pulses. An optical delivery system may be coupled to the sub-nanosecond laser source to receive and direct the treatment beam. A processor may be coupled to the sub-nanosecond laser source and the optical delivery system. The processor may include a tangible non-volatile computer readable medium including instructions to determine a lens cut pattern from a posterior to an anterior of the lens for lens fragmentation. A plurality of energies of the treatment beam may be scaled as a function of a depth of the lens cut pattern to maintain a bubble volume formed by the single pulse of treatment beam. The treatment beam may be output according to the lens cut pattern and the determined energies.

In some variations, the plurality of energies may be scaled linearly with a depth of the lens cut pattern. The energy of the treatment beam may decrease as a function of the depth of the lens linearly from the posterior to the anterior of the lens. The energy of the treatment beam at the posterior of the lens may be between twice an energy threshold and ten times an energy threshold. The energy threshold may be an energy level at which visible damage in tissue is first observed.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
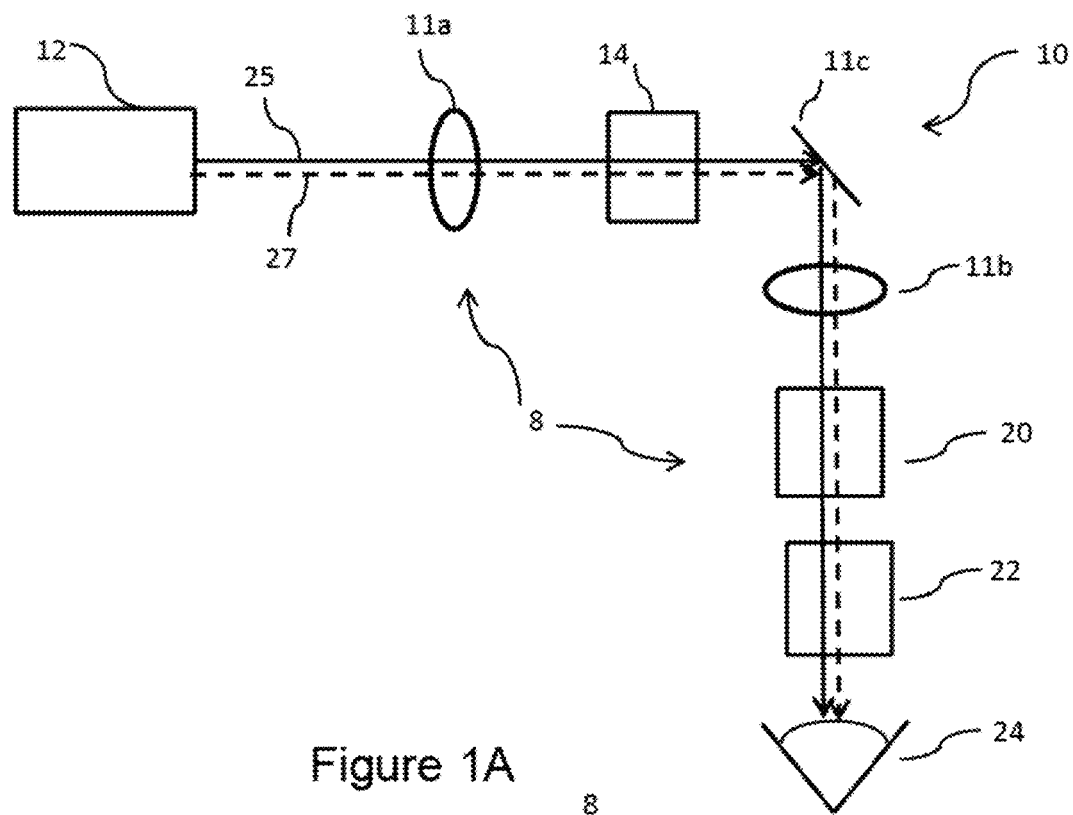
FIG. 1A is a schematic diagram of the optical path having a single optical path for high and low energy pulsed laser beams according to many embodiments.

The embodiments described herein are particularly well suited for treating tissue, such as the surgical treatment of tissue. In many embodiments, the tissue comprises an optically transmissive tissue, such as tissue of an eye. The embodiments as described herein can be particularly well suited for increasing the quality of the cutting of the material such as eye tissue and to provide for incisions of numerous different eye tissues at various locations within the eye, as well as fragmentation of the crystalline of lens for removal during a cataract procedure.

In many embodiments, methods and systems related to laser eye surgery are disclosed. A laser is used to form incisions in the cornea, in the lens capsule, and/or in the crystalline lens nucleus. In many embodiments, a laser eye surgery system includes a laser source to produce a pulsed laser treatment beam to incise tissue within the eye, an imaging system to measure the spatial disposition of external and internal structures of the eye in which incisions can be formed, a scanning assembly operable to scan the treatment beam, and can include a video subsystem that can be used to, for example, provide images of the eye during docking of the eye to the laser eye surgery system and also provide images of the eye once the docking process is complete. In many embodiments, a liquid interface is used between a patient interface lens and the eye. The use of the liquid interface avoids imparting undesirable forces to the patient's eye.

In many embodiments, improved laser eye surgery systems, and related methods, are provided. In these embodiments, the laser eye surgery systems provided herein perform multiple aspects of laser cataract surgery, including the use a single laser source to form precise incisions in the cornea, lens capsule, crystalline lens nucleus and further to perform lens fragmentation of the crystalline nucleus. In many embodiments, the single laser source is also used for imaging various tissues within the eye, including the cornea, the anterior portion of the lens, and in some embodiments, the posterior portion of the lens.

Although specific reference is made to tissue cutting for laser eye surgery, embodiments as described herein can be used in one or more of many ways with many surgical procedures and devices, such as orthopedic surgery, robotic surgery and microkeratomes.

In many of the embodiments described herein, a system for laser ophthalmic surgery on an eye of a patient comprises: a single laser source, under the operative control of a controller, configured to alternatively deliver a first treatment laser beam and a second treatment laser beam, each treatment laser beam comprising a plurality of laser pulses, the first treatment laser beam having a pulse energy of about 10 to 500 µJ and the second pulsed laser beam having a second pulse energy of about 0.1 to 10 µJ and lower than the first treatment laser beam; and an optical system operatively coupled to the laser source by the controller and configured to focus the first treatment laser beam to a first focal spot and direct the first focal spot in a first treatment pattern into one or more intraocular targets, including a first intraocular target. The optical system is further configured to focus the second treatment laser beam to a second focal spot and direct the second focal spot in a second treatment pattern into the one or more intraocular targets, including a second intraocular target. The first intraocular target is different than the second intraocular target.

In many embodiments, a method for laser ophthalmic surgery on an eye of a patient comprises: alternatively delivering, using a single laser source, a first treatment laser beam and a second treatment laser beam, each treatment laser beam comprising a plurality of laser pulses, focusing the first treatment laser beam to a first focal spot and directing the first focal spot in a first treatment pattern into one or more intraocular targets, including a first intraocular target; and focusing the second treatment laser beam to a second focal spot and directing the second focal spot in a second treatment pattern into the one or more intraocular targets, including a second intraocular target. The first treatment laser beam has a pulse energy of about 10 to 500 µJ and the second pulsed laser beam has a second pulse energy of about 0.1 to 10 µJ and is lower than the first treatment laser beam. The first intraocular target is different than the second intraocular target.

In many embodiments, the one or more intraocular targets may be selected from the group consisting of a cornea, a limbus, a sclera, an anterior portion of a lens capsule, a crystalline lens, a posterior portion of the lens capsule, and a synthetic intraocular lens implant.

In many embodiments, a laser ophthalmic surgery system is provided and includes a sub-nanosecond pulsed laser source, preferably a single laser source, configured to generate at least two treatment laser beams having different laser pulse properties. In many embodiments, the at least two treatment laser beams include: (1) a first treatment laser beam having a pulse energy of between about 10 to 500 µJ and preferably a repetition rate of between about 1 to 50 KHz (which may be referred to herein as the "higher energy treatment beam"); and (2) a second treatment laser beam having a lower pulse energy than the first treatment laser beam of between about 0.1 to 10 µJ and preferably a higher repetition rate than the first laser beam of between about 50 to 200 KHz (which may referred to herein as the "lower energy treatment beam").

The pulse duration of the higher energy treatment beam may be the same or different as the pulse energy of the lower energy treatment beam. In many embodiments, the pulse duration of each of the at least two treatment laser beams, whether the same or different, is preferably less than about 1 nanosecond, preferably less than or equal to 500 ps, more preferably less than or equal to 250 ps, and preferably less than or equal 150 ps. Preferably, the pulse duration of each of the laser beams is less than or equal to 150 ps. Preferably, the pulse duration of the each of the at least two laser beams is greater than 10 fs, or greater than 100 fs, or greater than 500 fs or greater than 999 fs. Preferably the pulse duration In many embodiments, the wavelengths of each of the pulsed treatment laser beams is independently selected from the group consisting of infrared wavelength pulses, visible wavelength pulses and ultraviolet wavelength pulses. The wavelengths of the higher energy treatment beam and the low energy treatment beams may be the same or different; however, preferably the wavelengths are different. When an infrared wavelength is selected, the wavelength of the treatment beam is preferably between about 870 nm and 1200 nm, or between about 1000 nm and 1150 nm, preferably about 1050 nm to 1100 nm. In some embodiments, the wavelength of an infrared wavelength treatment beam is 1064 nm. When a visible wavelength is selected, the wavelength of the treatment beam is preferably between about 450 nm and 869 nm, or between about 475 nm and 600 nm, preferably about 500 nm and 550 nm. In some embodiments, the wavelength of a visible wavelength laser beam is 532 nm. When an ultraviolet wavelength is selected, the wavelength of the treatment laser beam is preferably between about 275 nm and 449 nm, or between about 300 nm and 420 nm, preferably about 320 nm and 370 nm. In some embodiments, the wavelength of an ultraviolet wavelength laser beam is 355 nm.

In many embodiment, the wavelength of the higher energy treatment beam is an infrared wavelength, and the wavelength is preferably between about 1050 nm to 1100 nm. In some embodiments, the wavelength of the higher energy treatment beam is 1064 nm.

In many embodiment, the wavelength of the lower energy treatment beam is an ultraviolet wavelength, and the wavelength is preferably between 300 nm and 420 nm, preferably about 320 nm and 370 nm. In some embodiments, the wavelength of the lower energy treatment beam is 355 nm.

In many embodiments, the wavelength of the higher energy treatment beam is different than, preferably longer than, the wavelength of the lower energy treatment beam. In many embodiments, the wavelength of the higher energy treatment beam is an infrared wavelength and the wavelength of the lower energy treatment beam is ultraviolet.

The pulsed laser source is preferably a single laser source, and the different laser beams correspond to the first, second or third harmonic of the pulsed laser beam. In many preferred embodiments, the first harmonic is an infrared wavelength pulsed laser beam, the second harmonic is a visible wavelength pulsed laser beam third harmonic is an ultraviolet wavelength laser beam. In many embodiments the single laser source is a pulsed ND:YAG laser having a first harmonic of 1064 nm, a second harmonic of 532 nm, and a third harmonic of 355 nm.

In a preferred embodiment, the laser source is configured to generate two different laser beams having the following properties:
1. A higher energy treatment beam is an infrared wavelength beam with a wavelength between 1050 nm to 1100 nm, preferably 1064 nm, a pulse energy of between about 10 and 500 µJ and repetition rate of between about 1 and 50 KHz; and
2. A lower energy treatment beam is an ultraviolet wavelength beam with a wavelength of between 320 nm and 370 nm, preferably 355 nm, a pulse energy of between about 0.1 and 10 µJ and repetition rate 50 to 200 KHz.

The precision of a treatment beam for making incisions in laser ophthalmic surgery is dependent on wavelength, spot size and Rayleigh scattering of the treatment beam. For instance, the ultraviolet harmonic of a YAG laser source is more precise than the corresponding first harmonic infrared wavelength of the YAG laser source because the ultraviolet wavelength is ⅓ the wavelength. ⅓ of the spot size, and ⅓ of the Rayleigh Range of the infrared harmonic (spot size being linearly dependent on wavelength). In the present invention, the use of at least two different treatment beams having different wavelengths therefore provide two different treatment beams of different precision: (1) a lower energy treatment beam having a wavelength, preferably an ultraviolet wavelength, capable of higher precision incisions, (2) and a higher energy treatment beam having a wavelength, preferably an infrared wavelength, useful for lower precision incision. The lower energy treatment beam can be used for incisions which require high precision, such as corneal incisions and capsulotomy incisions in cataract surgery. Conversely, the lower precision, higher energy treatment beam can be used, for instance, for lens fragmentation during cataract surgery.

The systems and methods of the present invention preferably include one or more imaging systems for imaging the one or more ocular targets. Although many different imaging techniques may be used in different embodiments, a confocal imaging based on pulsed laser raster scanning of the tissue to be treated may be preferred. The imaging system may also preferably include video.

In embodiments of the present invention that include confocal imaging, it is preferable to select higher energy treatment beams and lower energy treatment beams that have different wavelengths. Since successful imaging of different ocular tissues in an eye depends on the wavelength of the light used for the imaging, the use of different wavelengths for each allows for imaging different regions and areas of eye. For instance, ultraviolet wavelengths are particularly well suited to confocal imaging of cornea and lens anterior up to about 150 microns from the anterior cornea. The use of infrared wavelengths allows confocal imaging of the posterior portion of the lens because the infrared light penetrates to the lens posterior. Thus, in many embodiments that include imaging, the wavelength of the higher energy treatment beam is an infrared wavelength, and the wavelength is preferably between about 1050 nm to 1100 nm. In some embodiments, the wavelength of the higher energy treatment beam is 1064 nm. The wavelength of the lower energy treatment beam is an ultraviolet wavelength, and the wavelength is preferably between 300 nm and 420 nm, preferably about 320 nm and 370 nm. In some embodiments, the wavelength of the lower energy treatment beam is 355 nm.

In other embodiments, the higher energy treatment beam is a visible wavelength treatment beam to improve imaging by improving scattering that relatively low at infrared wavelengths. Since scattering is related to $1/\lambda^4$, the cornea can be clearly imaged with the ultraviolet wavelength because the wavelength is relatively short but the scattering is correspondingly high. However, with infrared wavelengths, scattering becomes correspondingly low. Therefore, with infrared wavelengths the cornea can be imaged, the anterior of the lens can be imaged, and the posterior lens can be imaged, but images may be of lower quality.

Since infrared wavelengths can result in low quality images, the higher energy treatment beam may be converted to a visible wavelength prior to imaging of the one or more intraocular targets. Preferably, the wavelength of the visible wavelength is green. The visible wavelength allows one increase in signal intensity significantly from the Mies scattering, and enables improved images of the lens.

Preferably, the imaging systems and methods included herein include imaging of one or more areas of the posterior lens capsule. However, this is not strictly necessary. Even imaging of posterior lens capsule, it is possible to measure thickness of the lens thickness prior to surgery, which can be is input into the system and read by the controller. One can then image the anterior lens capsule according to the methods described herein, and together with the thickness of the lens measured pre-surgically (and adding a suitable safety factor tolerance), the complete lens structure can be modeled according.

The arrangement of the confocal imaging system depends on the configuration of the optical path. In many embodiments of a system for laser ophthalmic surgery, both treatment patterns are conducted along the same optical path from the light source to the eye in the direction of propagation of the laser beam. Thus, in many embodiments, the optical system comprises an objective lens, and optical system is configured to direct both the first treatment laser beam and the second treatment laser beam along a same optical path from the laser source to the objective lens. In these embodiments, the laser source is configured to alternatively deliver a first probe laser beam corresponding to the first treatment laser beam and a second probe laser beam corresponding to the second treatment laser beam. The first probe laser beam may be obtained, for instance, by attenuating the first treatment beam. The second probe laser beam may be obtained, for instance, by attenuating second treatment beam. An imaging system operatively coupled to the laser source and optical system by the controller is configured to direct the first probe laser beam to the at least one or more intraocular targets and to confocally detect back reflected light of the first probe laser beam along the optical path from the at least one or more intraocular targets, thereby obtaining first image data corresponding a first area of the one or more intraocular targets. The imaging system is also configured to direct the second probe laser beam to the at least one or more intraocular targets and to confocally detect back reflected light of the probe laser beam from the at least one or more intraocular targets back along the optical path, thereby obtaining second image data corresponding to a second area of the one or more intraocular targets. The first area is different from the second area.

In these embodiments, a method for laser ophthalmic surgery comprises: directing both the first treatment laser beam and the second treatment laser beam along a same optical path from the laser source to the objective lens in a direction of propagation of the first and second laser beams. The method may also comprise: alternatively delivering a first probe laser beam corresponding to the first treatment laser beam and a second probe laser beam corresponding to the second treatment laser beam; directing the first probe laser beam to the at least one or more intraocular targets and confocally detecting back reflected light of the first probe laser beam from the at least one or more intraocular targets, thereby obtaining first image data corresponding a first area of the one or more intraocular targets; and directing the second probe laser beam to the at least one or more intraocular targets and confocally detecting back reflected light of the probe laser beam from the at least one or more intraocular targets, thereby obtaining second image data corresponding to a second area of the one or more intraocular targets. The first area is different from the second area.

In another embodiment of a system for laser ophthalmic surgery, the first treatment beam and the second treatment beam are delivered along different optical path segments in a direction of propagation of the light beam in a direction of propagation from the laser source to the objective lens. In these embodiments, the optical path is configured to separate the first and second treatment laser beams so as to divert the first treatment laser beam along a first optical path segment, to divert the second treatment laser beam along a different, second optical path segment and to recombine the first and second probe laser beams prior to passing through an objective lens. In many of these embodiments, the laser source is configured to alternatively deliver a first probe laser beam corresponding to the first treatment laser beam and a second probe laser beam corresponding to the second treatment laser beam. The first probe laser beam may be obtained, for instance, by attenuating the first treatment beam. The second probe laser beam may be obtained, for instance, by attenuating second treatment beam. A first imaging system is operatively coupled to the laser source and the optical system by the controller and configured to direct the first probe laser beam to the at least one or more intraocular targets and to confocally detect back reflected light of the first probe laser beam from the at least one or more intraocular targets back directed along the first optical path segment, thereby obtaining first image data corresponding a first area of the one or more intraocular targets. A second imaging system operatively coupled to the laser source and optical system by the controller and configured to direct the second probe laser beam to the at least one or more intraocular targets and to confocally detect back reflected light of the second probe laser beam from the at least one or more intraocular targets along the second optical path segment, thereby obtaining second image data corresponding a second area of the one or more intraocular targets. The first area is different from the second area.

The method comprises separating the first and second treatment laser beams, thereby diverting the first treatment laser beam along a first optical path segment, diverting the second treatment laser beam along a different, second optical path segment and recombining and directing the first and second probe laser beams along a same optical path prior to passing through an objective lens. The method may further comprise: alternatively delivering a first probe laser beam corresponding to the first treatment laser beam and a second probe laser beam corresponding to the second treatment laser beam; directing the first probe laser beam to the at least one or more intraocular targets and confocally detecting back reflected light of the first probe laser beam from the at least one or more intraocular targets back directed along the first optical path segment, thereby obtaining first image data corresponding a first area of the one or more intraocular targets; and directing the second probe laser beam to the at least one or more intraocular targets and confocally detecting back reflected light of the second probe laser beam from the at least one or more intraocular targets along the second optical path segment, thereby obtaining second image data corresponding a second area of the one or more intraocular targets, The first area is different from the second area.

In many embodiments, the one or more intraocular targets may be selected from the group consisting of a cornea, a limbus, a sclera, an anterior portion of a lens capsule, a crystalline lens, a posterior portion of the lens capsule, and a synthetic intraocular lens implant. The first and second areas may be a portion of the selected ones of the cornea, the limbus, the sclera, the anterior portion of a lens capsule, the crystalline lens, the posterior portion of the lens capsule, and the synthetic intraocular lens implant.

Thus, in many embodiments, imaging of the eye includes confocally imaging one or more portions of the ocular targets to be treated. Any suitable device, assembly, and/or system, such as described herein, can be used to confocally image one or more portions of the eye or other tissue to be imaged. The confocal imaging methods used herein generally include using the laser source to generate one or more probe beams; propagating the one or more probe beams to a scanner along an optical path to the eye; focusing the one or more probe beams to a focal point at a location within the eye; using the scanner to scan, preferably raster scan, the focal point to different locations within the eye; propagating a portion of the probe beam reflected from the focal point location back along the optical path to a sensor; and generating an intensity signal indicative of the intensity of a portion of the electromagnetic radiation beam reflected from the focal point location and propagated to the sensor. The method can include modifying polarization of at least one of the electromagnetic radiation beam and a portion of the electromagnetic radiation beam reflected from the focal point location. The method can include using the polarization-sensitive device to reflect a portion of the electromagnetic radiation beam reflected from the focal point location so as to be incident upon the sensor.

A raster scan may be defined as a 3-dimensional tracing of a laser light source along the object to be imaged. In many embodiments, the raster scan is a scan pattern in which the laser light source is swept continuously along an area to be imaged, scanned from side to side in lines from top to bottom in in a planar section, and then repeated in depth wise steps in the tissue to be imaged. When used in connection with a pulsed laser source, a pattern of closely spaced confocal intensity measurements resulting from separate laser pulses may be used to form an image.

A raster scan is preferably comprised of laser pulses spaced at intervals. In many embodiment, each spot at the ocular tissue irradiated by a laser pulse represents a confocal intensity measurement, each spot having its origin as a separate laser pulse. The distance between each spot is a function of the sweep speed of the laser light source along the imaging path and the pulse repetition rate of the laser surgical system. In ophthalmic applications of confocal imaging, the pulse repetition frequency of the laser source can generally vary from 10 kHz to 250 kHz, or alternatively, between 50 to 200 kHz, or between 75 to 150 kHz.

In a preferred embodiment, image data is collected on a point by point (i.e., pixel by pixel) basis by raster scanning the focus of a pulsed laser beam across a surface of the tissue to be imaged and detecting an intensity signal for each laser pulse corresponding to an intensity of, for instance, the light reflected from the location each laser pulse was respectively focused. The intensity of the light measured may alternatively be intensity of the light emitted by the tissue to be imaged either by fluorescence or phosphorescence of the target tissue after irradiation by the laser light beam. The resulting image data may comprise a set of data points, P, such as pixels, each data point p in the data corresponding to a unique, discrete location (x,y, and z) within the object to be issued and having an associated intensity, I, at the location. These data points may be referred to herein as image data. The set of data points therefore generally comprise at least one location datum and one intensity datum. The location of the laser pulses at coordinates (x,y,z) are connected in 3D space along the predetermined raster scan pattern, the design of which is delimited by the velocities and accelerations of the mirrors that are generating the trajectory of the laser scan.

The laser source is configured to alternatively deliver a first probe laser beam corresponding to the first treatment laser beam and a second probe laser beam corresponding to the second treatment laser beam. When a confocal imaging arrangement is used, the treatment laser beams (i.e. the laser beam having the parameters suitably chosen as described above for the modification of tissue) are preferably attenuated to the nanoJoule level and to produce corresponding probe beams used for imaging of the respective structures to be imaged. When used for imaging, the attenuated laser beams may be referred to as an imaging or "probe" beams. In many embodiments, the treatment beams and the probe beams may be the same except for the pulse energy of the laser source is lower than the treatment beam when the laser beam is used for imaging. In many embodiments, the pulse energy of the laser beams when used for imaging is preferably from about 0.1 nJ to 10 nJ, preferably less than 2 nJ and more preferably less than 1.8 nJ. The use of the same laser beam for both treatment and imaging provides for the most direct correlation between the position of the focal locations for imaging and treatment—they are the same beam. This attenuated probe beams are preferably used directly in a back reflectance measuring configuration, but, alternatively, may be used indirectly in a fluorescence detection scheme. Since increases in both backscatter and fluorescence within tissue structures will be evident, both approaches have merit.

In a preferred embodiment, imaging of a first target area to be modified is performed sequentially with the modification of the tissue in the first target area before moving on to a second, different, target area, i.e. imaging is performed sequentially with treatment in a predetermined target area. Thus, for instance imaging of the lens capsule is preferably followed by treatment of the lens capsule before imaging is carried out on other either structures, such as the cornea or the crystalline lens. In another embodiment, imaging of a first target area where a first incision to be place is performed sequentially with the scanning the treatment beam to perform the incision in the first target area before moving on to a second target area for performing a second incision, i.e. imaging of the area to be incised is performed sequentially with scanning the treatment beam to perform in the predetermined target area.

The systems and methods of the present invention may suitably be applied to cataract surgery. Thus, in many embodiments, the methods and/or systems described herein are used in cataract surgery using a laser eye surgery system for verifying the placement of incisions in a cataract surgery.

In cataract surgery, a capsulotomy incision, often in the form of a small round hole is formed in the anterior side of the lens capsule to provide access to the lens nucleus. In addition, cataract surgery may include three types of corneal incisions: arcuate incisions, primary incisions ("primary cataract incisions" or simply "cataract incisions") and sideport incisions. Primary incisions and sideport incisions may have the same structure. They are generally multiplanar structures that create an opening that allow the doctor physician access into the anterior chamber. The primaries are used for insertion of the aspiration tool and the insertion of the IOL. Sideport incisions may be used for inserting smaller instrumentation into the anterior chamber. The location and shape of both the primary incisions and the sideport incisions are determined by the user parameters and, optionally, by information from a section scan as described herein, where the cornea anterior and posterior surfaces may be modeled by circles. The anterior and posterior curvatures of the cornea as measured in the circular fits of the section scans may optionally be used to position the cuts.

Arcuate incisions may be used to correct a patient's astigmatism. For instance, they may adjust the curvature of the cornea to a more spherical shape by means relaxing stresses along the meridian on which they are placed. They are parts of a conical surface that crosses both the anterior and posterior surfaces of the cornea. In some embodiments, the anterior curvature and posterior curvature of the cornea, as measured in a circular fit to a section scan, is are used to position an "along-the-cut" scan. The along-the-cut scan lays on the surface of a cone that transverses the cornea. The arcuate incision can be located within the along-the-cut scan.

The laser surgery system can be used to form any suitably shaped capsulotomy. For example, while the anterior and posterior capsulotomies are often circular, any other suitable shape, including but not limited to, elliptical, rectangular, and polygonal can be formed. And the anterior and/or posterior capsulotomy can be shaped to accommodate any correspondingly suitably shaped IOL.

For example, the laser surgery system can be used to incise an anterior capsulotomy and/or a posterior capsulotomy in the anterior portion of a lens capsule. The lower energy treatment laser beam is preferably used for an anterior capsulotomy. The focal point of the lower energy treatment beam can be scanned to form an anterior capsulotomy that transects the anterior portion of the lens capsule. Likewise, the focal point of the higher energy treatment beam can be scanned to form a posterior capsulotomy closed incision boundary surface that transects the posterior portion of the lens capsule.

The anterior and/or posterior incision boundaries can be designated using any suitable approach. For example, a plan view of the patient's eye can be obtained using a camera. A capsulotomy incision boundary can be located and shown superimposed on the plan view of the patient's eye to illustrate the size, location, and shape of a planned capsulotomy relative to the patient's eye. The capsulotomy incision boundary can be manually defined by an operator of the laser surgery system and/or the laser surgery system can be configured to generate an initial capsulotomy incision boundary for operator verification and/or modification.

The laser surgery system can also be used to form any suitably shaped arcuate, primary or sideport incisions. Corneal incisions in a cataract procedure are preferably formed using the low energy treatment beam.

In many embodiments, a cataract procedure comprises a capsulotomy incision, at least one corneal incision and lens fragmentation. In one embodiment, imaging of the target tissue where the capsulotomy is to be performed is carried out by the attenuated lower energy treatment beam followed by scanning of the lower energy treatment beam to perform the capsulotomy. Imaging by the attenuated lower energy treatment beam of the corneal target tissue where the at least one corneal incision is to be placed is carried out and then the low energy treatment beam is scanned to perform the at least one of the corneal incision. Imaging by the attenuated higher energy treatment beam of the lens target tissue where the lens fragmentation is to be placed is carried out and then the higher energy treatment beam is scanned to perform the at least one of the corneal incision.

In many embodiments, the methods and systems may include confocally imaging a cornea by scanning one or more of portions of the cornea where a cataract incision, sideport incision or arcuate incision is to be placed using the lower energy treatment beam. In a preferred embodiment, one sectional image of the cornea is performed for each selected corneal incision. These images are preferably in the form of a section scan. Preferably, a section scan comprises a raster scan of a pulsed laser beam along the cornea, including the anterior surface and posterior surface, on a vertical plane centered at the cornea incision center and oriented along an incision's meridian. The trajectory preferably goes from deep to shallow, inside the eye, crossing the cornea. The posterior and anterior boundaries of the cornea may be identified in the image by, for instance, Dijkstra segmentation of the image, and the resulting image may be provided to the user.

If the selected corneal incision is an arcuate incision, an "along-the-cut" imaging scan is also preferably performed. An along-the-cut imaging scan may assist a physician in choosing the correct location for the arcuate incision in order to maintain an adequate depth and avoid posterior penetration. The "along the cut" scan preferably has the same conical shape as the arcuate incision and is inclusive of the entire area to be covered arcuate incision. The conical sector in the "along the cut" scan is mapped into a rectangular domain 520 defined by the conical coordinates. The resulting conical image is segmented and fit. Optionally, the resulting fits to the anterior and posterior surfaces of the cornea are used to construct the arcuates, which can then are overlaid on their sections and "along the cut" scans After the relevant portions of the lens, lens capsule and cornea have been imaged, the incisions defined by the physician parameters may be projected onto the image, and a treatment pattern scan of the laser light beam is generated. The treatment pattern scan preferably consists of a continuous set of x, y, z points arranged in space that are designed to carry out the incisions defined by the user. The location of the treatment scans may be projected onto at least one of the video and confocal images in order to define the set of expected scan locations of the incisions.

Figure 1B:
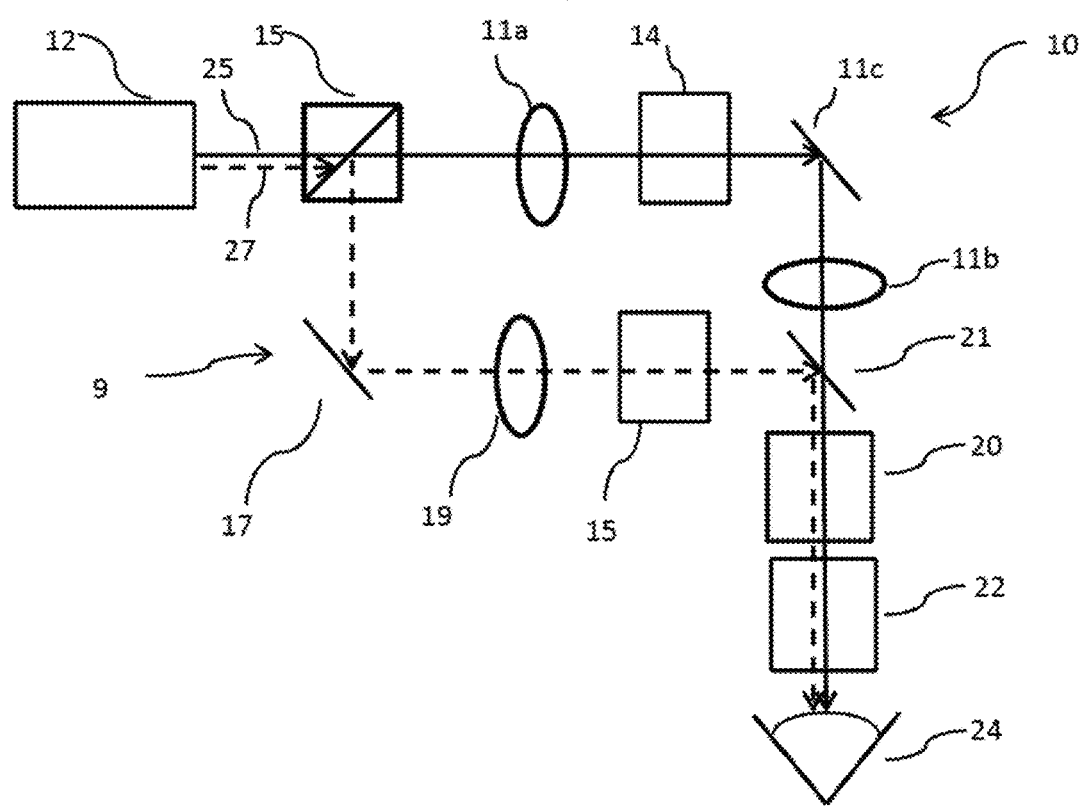
FIG. 1B is a schematic diagram of the optical path having a branched optical path for high and low energy pulsed laser beams according to many embodiments.

Schematic diagrams of arrangement of various components of a laser surgical system according to many embodiments are shown in FIGS. 1A and 1B. FIG. 1A shows a configuration of an optical path in which a higher pulse energy laser beam 25 and a lower energy pulsed laser beam 27 are both directed along a same optical path 8 from the single laser source 12 to an eye 24 of a patient. FIG. 1B shows a configuration in which a higher pulse energy laser beam 25 and a lower pulse energy treatment beam 27 are directed along separate optical path 8, 9.

The various components placed along the optical paths 8,9 of the laser surgery systems shown in FIGS. 1A and 1B include: a laser source/assembly 12, preferably a single laser source/assembly 12 configured to reversibly emit a higher pulse energy laser beam 25 and a lower pulse energy laser beam 27; various optical elements 11a, 11b, 11c, 17, 19 configured to direct laser beams 25, 27 from the laser source 12 to the eye 24; an optical element 15 configured to direct laser beams 25 and 27 generally based on wavelength along separate optical path 8,9; optional confocal detection assemblies 14, 15, an objective lens assembly 20, and an optional patient interface device 22. An optical delivery system, including optical paths 8 and 9 for receiving and directing the treatment beam may comprise some or all of these components coupled to the to the sub-nanosecond laser assembly 12, all or some portion thereof under the operative control of a controller.

In an embodiment in which the high and low energy laser beams are directed along a same optical path, as shown in FIG. 1A, a laser source/assembly 12, preferably a single laser source/assembly 12 is configured to reversibly emit a higher pulse energy laser beam 25 and a lower pulse energy laser beam 27. In many preferred embodiments, the higher pulse energy laser beam 25 is an infrared wavelength beam and the lower pulse energy laser beam is an ultraviolet wavelength laser beam. Although laser beams 25, 27 are shown for illustration purposes as being displaced physically from each other, it should be understood that both beams preferably exit laser source 12 at the same position and with the same direction. As would be understood by those ordinarily skilled, laser source manufacturers can be supply a laser source in which with appropriate specifications of the exit location of laser beams 25, 27.

Upon exiting laser source/assembly 12, laser beams 25, 27 are guided along optical path 8 by one or more optical elements 11a, 11b, 11c, which may be, for instance, mirrors or lenses. In some or more embodiments, optical elements 11a, 11b, or 11c may be optionally chosen to differently guide laser beams 25, 27 to ensure that they are appropriately conducted along optical path 8 to object lens assembly 20 and eye 24.

FIG. 1B shows a configuration in which a higher pulse energy laser beam 25 and a lower pulse energy treatment beam 27 are directed along separate optical path 8, 9. Upon exiting laser source/assembly 12, laser beams 25, 27 are directed to an optical element which is capable of splitting laser beams 25, 27 along different optical paths. Beam splitting optical element 15 directs higher pulse energy treatment beam 25 along a first optical path 8, and also directs the lower pulse energy treatment beam along second optical path 9. Beam combining optical element 21 preferably combines higher pulse energy treatment beam 25 and lower pulse energy treatment beam 27 prior to the object lens 20 and before being directed to eye 24. Laser beam 25 is guided along optical path 8 by one or more optical elements 11a, 11b, 11c, which may be, for instance, mirrors or lenses. Optical elements 11a, 11b, or 11c guide laser beam 25 along optical path 8 to the beam combining optical element 21 and subsequently to object lens assembly 20 and eye 24. A first confocal imaging assembly 14 is preferably optimized for imaging with higher pulse energy treatment beam 25 and is configured to detect back reflected light of higher pulse energy treatment beam 25 from eye 24.

In FIG. 2B, lower pulse energy treatment beam 27 is guided along optical path 9 by one or more optical elements 17, 19, which may be, for instance, mirrors or lenses. Optical elements 17, 19 guide laser beam 27 along optical path 9 to the beam combining optical element 21 and subsequently to object lens assembly 20 and eye 24. A second confocal imaging assembly 15 is preferably optimized for imaging with lower pulse energy treatment beam 27 and, in many embodiments, is configured to detect back reflected light of higher pulse energy treatment beam 27 from eye 24.

Figure 2:
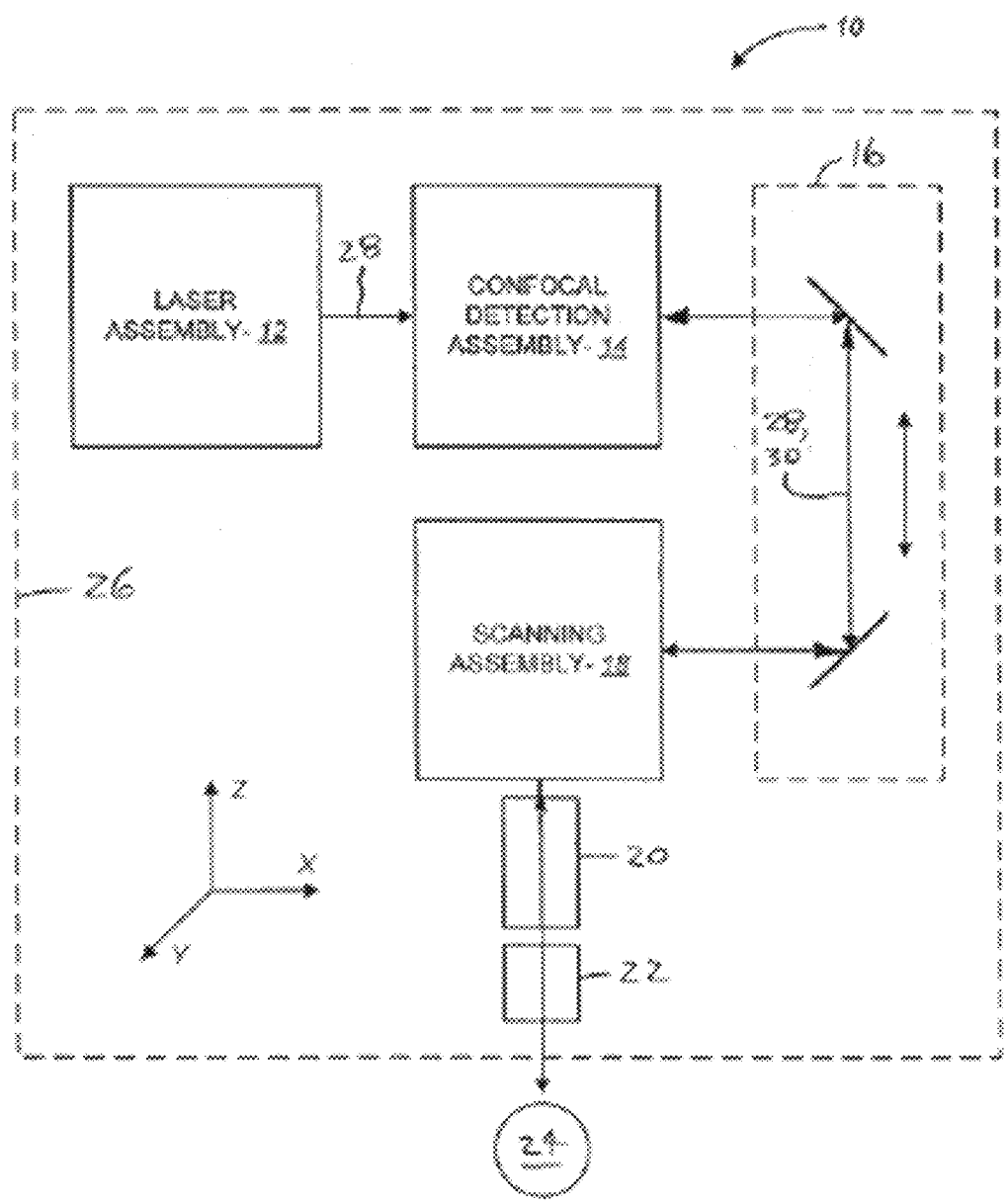
FIG. 2 is a schematic diagram of a laser surgery system, in accordance with many embodiments.
Figure 3:
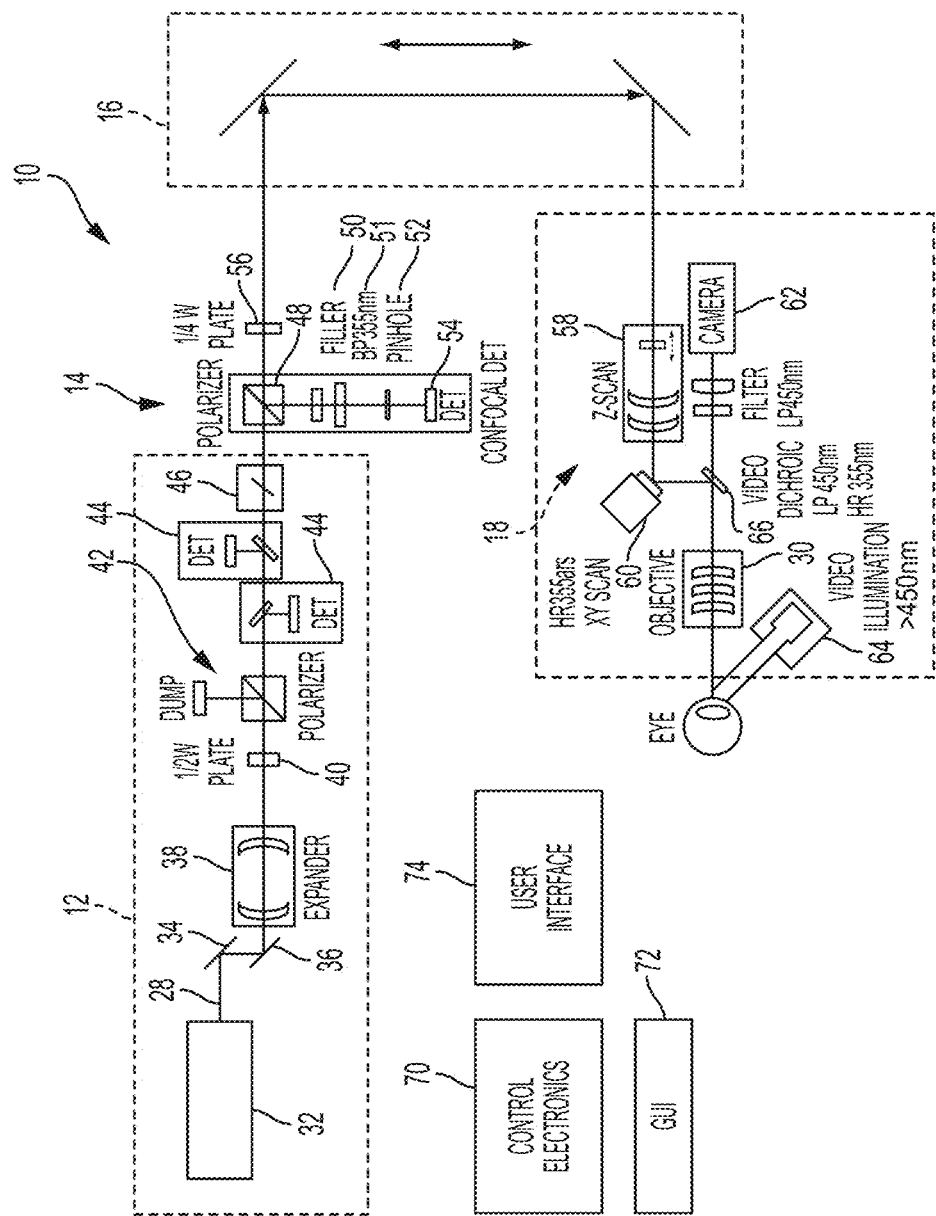
FIG. 3 is a schematic diagram of the laser surgery system of FIG. 2, in accordance with many embodiments.

FIG. 2 schematically illustrates a laser surgery system 10, according to many embodiments in which the higher energy treatment beam and the lower energy treatment beam are directed along a same optical path, and such as is shown in FIG. 1A. Although FIG. 2 shows a schematic for the laser surgery system 10 in which multiple laser beams are directed on a same optical path, the system can be modified to accommodate separate optical paths, such as those in FIG. 1B, based on the disclosures herein and the understanding of those ordinarily skilled.

Laser surgery system 10 may include a laser source/assembly 12, a confocal detection assembly 14, a free-floating mechanism 16, a scanning assembly 18, an objective lens assembly 20, and a patient interface device 22. The patient interface device 22 may be configured to interface with a patient 24. The patient interface device 22 may be supported by the objective lens assembly 20, which may be supported by the scanning assembly 18, which may be supported by the free-floating mechanism 16. The free-floating mechanism 16 may have a portion having a fixed position and orientation relative to the laser assembly 12 and the confocal detection assembly 14. An optical delivery system for receiving and directing the treatment beam may comprise some or all of the components coupled to the to the sub-nanosecond laser assembly 12.

In some embodiments, the patient interface device 22 can be configured to be coupled to an eye of the patient 24 using vacuum as described in co-pending U.S. patent application Ser. No. 14/068,994, entitled "Liquid Optical Interface for Laser Eye Surgery System," filed Oct. 31, 2013, the entire disclosure of which is incorporated herein by reference. The laser surgery system 10 can further optionally include a base assembly 26 that can be fixed in place or be repositionable. For example, the base assembly 26 can be supported by a support linkage that is configured to allow selective repositioning of the base assembly 26 relative to a patient and/or securing the base assembly 26 in a selected fixed position relative to the patient. Such a support linkage can be a fixed support base or a movable cart that can be repositioned to a suitable location adjacent to a patient. In many embodiments, the support linkage includes setup joints with each setup joint being configured to permit selective articulation of the setup joint, and can be selectively locked to prevent inadvertent articulation of the setup joint, thereby securing the base assembly 26 in a selected fixed position relative to the patient when the setup joints are locked.

In many embodiments, the laser assembly 12 is configured to emit an electromagnetic a higher pulse energy treatment beam and a lower pulse energy treatment beam. For ease of reference, energy radiation beam 28 shown in FIG. 2 may refer to either the higher pulse energy treatment beam or the lower energy treatment beam, when they are alternatively emitted. The beam 28, which may be the higher pulse energy treatment beam or the lower pulse energy treatment beam can include a series of laser pulses of any suitable energy level, duration, and repetition rate as described herein. In many embodiments, the laser assembly 12 incorporates sub-nanosecond laser technology where a short duration (e.g., approximately 10 ns to 1 picosecond in duration) laser pulse (with energy level in the tens of micro joules range) can be delivered to a tightly focused point to disrupt tissue, thereby substantially lowering the energy level required to image and/or modify an intraocular target as compared to laser pulses having longer durations. The laser assembly 12 may produce laser pulses having a wavelength suitable to treat and/or image tissue. For example, the laser assembly 12 can be configured to emit an electromagnetic radiation beam 28 such as that emitted by any of the laser surgery systems described in co-pending U.S. patent application Ser. No. 14/069,044, entitled "Laser Eye Surgery System," filed Oct. 31, 2013, and U.S. patent application Ser. No. 12/987,069, entitled "Method and System For Modifying Eye Tissue and Intraocular Lenses," filed Jan. 7, 2011, the full disclosures of which are incorporated herein by reference.

In some embodiments, the laser assembly may produce laser pulses having a wavelength of 355 nm with a numerical aperture NA in the range of 0.05 to 0.40, and preferably 0.15. The pulse length may be 0.6 ns with a pulse rate of 1 kHz to 1 mHz, and preferably 70 kHz to 100 kHz. Spot spacing may be from 6 um to 40 um.

The selection of NA may be based upon laser power, pulse rate, cut time, as well as safe incidental exposure levels of the iris and other ocular tissues not targeted by the cut. For instance, as the NA decreases, the laser power required increases. Also, the time needed for a cut of unit area (mm2) increases with increasing NA due to lower threshold energies. Therefore, increased NA tends to lead to an increased number of pulses and longer cut times.

In other varying embodiments, the laser assembly 12 may produce laser pulses having a wavelength between 800 nm to 1200 nm, and preferably between 1020 nm to 1050 nm. The pulse duration of the laser light can vary from 1 ps to 1000 ps. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 24 and specifically within the crystalline lens and the lens capsule of the eye is sufficient to produce optical breakdown and initiate visible damage in tissue. In yet another embodiment, the laser assembly 12 may have a diode-pumped solid-state configuration with a 1030 (+/−5) nm center wavelength. The laser assembly 12 can also include two or more lasers of any suitable configuration.

In many embodiments that include imaging, the wavelength of the higher energy treatment beam is an infrared wavelength, and the wavelength is preferably between about 1050 nm to 1100 nm. In some embodiments, the wavelength of the higher energy treatment beam is 1064 nm. The wavelength of the lower energy treatment beam is an ultraviolet wavelength, and the wavelength is preferably between 300 nm and 420 nm, preferably about 320 nm and 370 nm. In some embodiments, the wavelength of the lower energy treatment beam is 355 nm.

The laser assembly 12 may include control and conditioning components. In an embodiment, the control components may include a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. The conditioning components may include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 may have fixed positions relative to the base assembly 26. The beam 28 emitted by the laser assembly 12 may propagate along an optical path through the confocal detection assembly 14 to the free-floating mechanism 16. The beam 28 may propagate through the free-floating mechanism 16 along a variable optical path 30, which may deliver the beam 28 to the scanning assembly 18. In many embodiments, the beam 28 emitted by the laser assembly 12 may be collimated so that the beam 28 is not impacted by patient movement-induced changes in the length of the optical path between the laser assembly 12 and the scanner 18. The scanning assembly 18 may be operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and may be further operable to scan the location of a focal point of the beam 28 in the direction of propagation of the beam 28. The scanned beam may be emitted from the scanning assembly 18 to propagate through the objective lens assembly 20, through the interface device 22, and to the patient 24.

The free-floating mechanism 16 may be configured to accommodate a range of movement of the patient 24 relative to the laser assembly 12 and the confocal detection assembly 14 in one or more directions while maintaining alignment of the beam 28 emitted by the scanning assembly 18 with the patient 24. For example, the free-floating mechanism 16 may be configured to accommodate a range movement of the patient 24 in any direction defined by any combination of unit orthogonal directions (X, Y, and Z).

In some embodiments, the scanning assembly 18 can include a Z-scan device and an XY-scan device. The laser surgery system 10 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the patient 24. The scanning assembly 18 may be supported by the free-floating mechanism 16, which may accommodate patient movement, induced movement of the scanning assembly 18 relative to the laser assembly 12 and the confocal detection assembly 14 in three dimensions.

Because the patient interface device 22 may be interfaced with the patient 24, movement of the patient 24 may result in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 14, and optical components suitably coupled to the linkage so as to form the variable optical path 30. In an embodiment, the free-floating mechanism 16 can be configured as described in U.S. patent application Ser. No. 14/191,095 and PCT Application No. PCT/US2014/018752, filed Feb. 26, 2014 and entitled "Laser Surgery System," the entire disclosures of which are incorporated herein by reference.

A portion of electromagnetic radiation beam 28 may reflect from an eye tissue at the focal point and may propagate back to the confocal detection assembly 14. Specifically, a reflected portion of the electromagnetic radiation beam 28 may travel back through the patient interface device 22, back through the objective lens assembly 20, back through (and de-scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 may be directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, the posterior surface of the lens capsule, and so on. In many embodiments, the amount of the reflected electromagnetic radiation beam that travels to the confocal detection assembly 14 may be substantially independent of expected variations in the length of the variable optical path 30 due to patient movement, thereby enabling the ability to ignore patient movements when processing the intensity signal to image/locate structures of the eye.

The confocal detection assembly 14 may comprise a confocal imaging system which operates at the same wavelength as the electromagnetic radiation beam. The confocal imaging system combined with an inexpensive sub-nanosecond laser provides a cost effective and compact surgical system.

In many embodiments, the system 10 includes external communication connections. For example, the system 10 can include a network connection (e.g., an RJ45 network connection) for connecting the system 10 to a network. The network connection can be used to enable network printing of treatment reports, remote access to view system performance logs, and remote access to perform system diagnostics. The system 10 can include a video output port (e.g., HDMI) that can be used to output video of treatments performed by the system 10. The output video can be displayed on an external monitor for, for example, viewing and/or training. The output video can also be recorded for, for example, archival purposes. The system 10 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 may include an IR laser 32, alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the one-half wave plate 40 before passing through the polarizer 42. The beam exiting the polarizer 42 may be linearly polarized. The one-half wave plate 40 can rotate this polarization. The amount of light passing through the polarizer 42 depends on the angle of the rotation of the linear polarization. Therefore, the one-half wave plate 40 with the polarizer 42 may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

The system 10 can be set to locate the anterior and posterior surfaces of the lens capsule and cornea and ensure that the laser pulse beam 28 will be focused on the lens capsule and cornea at all points of the desired opening. In the embodiment of FIGS. 1 and 2, a confocal detection assembly 14 is described, although other modalities are within the scope of the present invention. Imaging modalities and techniques described herein, such as for example, Optical Coherence Tomography (OCT), Purkinje imaging, Scheimpflug imaging, structured light illumination, confocal back reflectance imaging, fluorescence imaging, or ultrasound may be used to determine the location and measure the thickness of the lens and lens capsule to provide greater precision to the laser focusing methods, including 2D and 3D patterning, or other known ophthalmic or medical imaging modalities and/or combinations thereof. An OCT scan of the eye will provide information about the axial location of the anterior and posterior lens capsule, the boundaries of the cataract nucleus, as well as the depth of the anterior chamber. This information is then be loaded into the control electronics 70, and used to program and control the subsequent laser-assisted surgical procedure. The information may also be used to determine a wide variety of parameters related to the procedure such as, for example, the upper and lower axial limits of the focal planes used for modifying the lens capsule, cornea, and synthetic intraocular lens implant, among others.

For instance, an optical coherence tomography (OCT) system may be used in place of the confocal imaging system. The OCT system is configured to produce a source beam used to locate one or more structures of the eye, such as by measuring the spatial disposition of eye structures in three dimensions. The measured eye structures can include the anterior and posterior surfaces of the cornea, the anterior and posterior portions of the lens capsule, the iris, and the limbus. As a non-limiting example, the system 10 can be configured to use an OCT imaging system employing wavelengths from 780 nm to 970 nm, or more particularly, from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

As shown in the illustrated embodiment, the scanning assembly 18 may include a Z-scan device 58 and an XY-scan device 60. The Z-scan device 58 may be operable to vary a convergence/divergence angle of the beam 28 and thereby change a location of the focal point in the direction of propagation of the beam 28. For example, the Z-scan device 58 may include one or more lenses that are controllably movable in the direction of propagation of the beam 28 to vary a convergence/divergence angle of the beam 28. The XY-scan device 60 may be operable to deflect the beam 28 in two dimensions transverse to the direction of propagation of the beam 28. For example, the XY-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown further in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

As should be appreciated, the laser surgery system 10 scans the eye with focal points of more than one electromagnetic radiation beam, where the electromagnetic radiation beams have varying degrees of polarization due to a varying wave plate orientation. The plurality of scans may compensate for imaging signal loss due to local cornea birefringence properties.

The system 10 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 10 and a fixed optical relay to transfer the laser pulses over a distance while accommodating laser pulse beam positional and/or directional variability, thereby providing increased tolerance for component variation.

The control electronics 70 controls the operation of and can receive input from the laser assembly 12, the confocal detection assembly 14, free-floating mechanism 16, the scanning assembly 18, the objective lens assembly 20, the patient interface 22, control panel/graphical user interface (GUI) 72, and user interface devices 74 via communication paths. The communication paths can be implemented in any suitable configuration, including any suitable shared or dedicated communication paths between the control electronics 70 and the respective system components.

The control electronics 70 can include any suitable components, such as one or more processors, one or more field-programmable gate array (FPGA), and one or more memory storage devices. The control electronics 70 is operatively coupled via the communication paths with the laser assembly 12, the confocal detection assembly 14, the free-floating mechanism 16, the scanning assembly 18, the control panel/GUI 72, and the user interface devices 74. In many embodiments, the control electronics 70 controls the control panel/GUI 72 to provide for pre-procedure planning according to user specified treatment parameters as well as to provide user control over the laser eye surgery procedure.

The control electronics 70 can include a processor/controller that is used to perform calculations related to system operation and provide control signals to the various system elements. A computer readable medium can be coupled to the processor in order to store data used by the processor and other system elements. The processor interacts with the other components of the system as described more fully throughout the present specification. In an embodiment, the memory can include a look up table that can be utilized to control one or more components of the laser system surgery system.

The processor can be a general purpose microprocessor configured to execute instructions and data such as a processor manufactured by the Intel Corporation of Santa Clara, California. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like. The memory can be local or distributed as appropriate to the particular application. Memory can include a number of memories including a main random access memory (RAM) for storage of instructions and data during program execution and a read only memory (ROM) in which fixed instructions are stored. Thus, the memory provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 74 can include any suitable user input/output device suitable to provide user input to the control electronics 70. For example, the user interface devices 74 can include devices such as a touch-screen display/input device, a keyboard, a footswitch, a keypad, a patient interface radio frequency identification (RFID) reader, an emergency stop button, a key switch, and so on.

Next, the characteristics of a cataract lens cut by the laser system 10 will be discussed. Received light is scattered by the clouding of a cataract lens. The higher the grade of the cataract, the more laser energy is needed to overcome the scattering and attenuation of the lens to deposit the beam energy at a desired location. Similarly, along an increasing depth of the cataract, the attenuation of beam energy will increase. For these reasons, a white cataract cannot be laser treated, but a semi-transparent cataract can be laser cut.

Increasing laser energy into a cataract lens may compensate for scattering losses at a given depth, but shallow layers of the lens are then treated with higher energy levels than desirable. For example, high laser energy deposition in grade 1-2 cataracts create large bubbles and high laser energy deposition in grade 2-4 cataracts propagate cracks in the lamellas. Therefore, simply increasing the energy level of a treatment beam into a lens will not improve lens fragmentation. For sub-nanosecond laser systems, a sensitive range of energies are available to cut a cataract cleanly without cracking. If the energy applied is small, incomplete separation of tissue results. If the energy applied is high, then excess collateral damage in the tissue appears and subsequent laser pulses scatter due to an irregular refraction index change. Furthermore, excessive energy will slow down the fragmentation procedure due to a maximum safe power of treatment.

The methods and systems described herein improve the consistency and quality of a laser fragmentation cut by adjusting the treatment energy to match the dynamic range of energies needed to form consistent cuts at different depths of the tissue for sub-nanosecond/infrared/picosecond lasers. For instance, some embodiments include an infrared (e.g., 1 us) laser assembly capable of performing both capsulotomy and lens fragmentation as described in detail below. This configuration further provides a cost-effective and efficient system where a single laser assembly is suitable for a plurality of surgical procedures.

Figure 4:
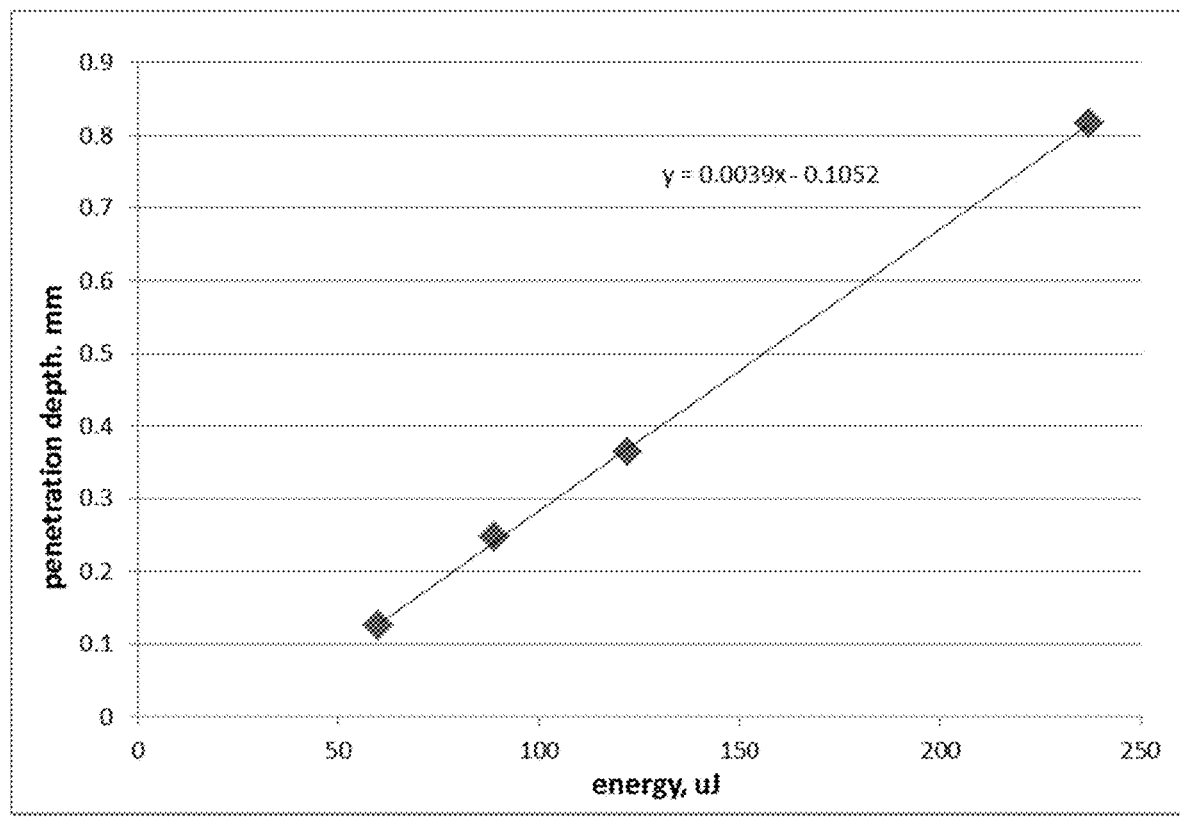
FIG. 4 is a graph illustrating penetration depth versus energy in a lens cut, in accordance with many embodiments.

FIG. 4 is a graph illustrating penetration depth versus energy in a lens cut, in accordance with many embodiments.

The greater the energy applied to the tissue, the higher the penetration depth of the cut. Specifically, penetration depth scales linearly with the energy of the beam.

Figure 5:
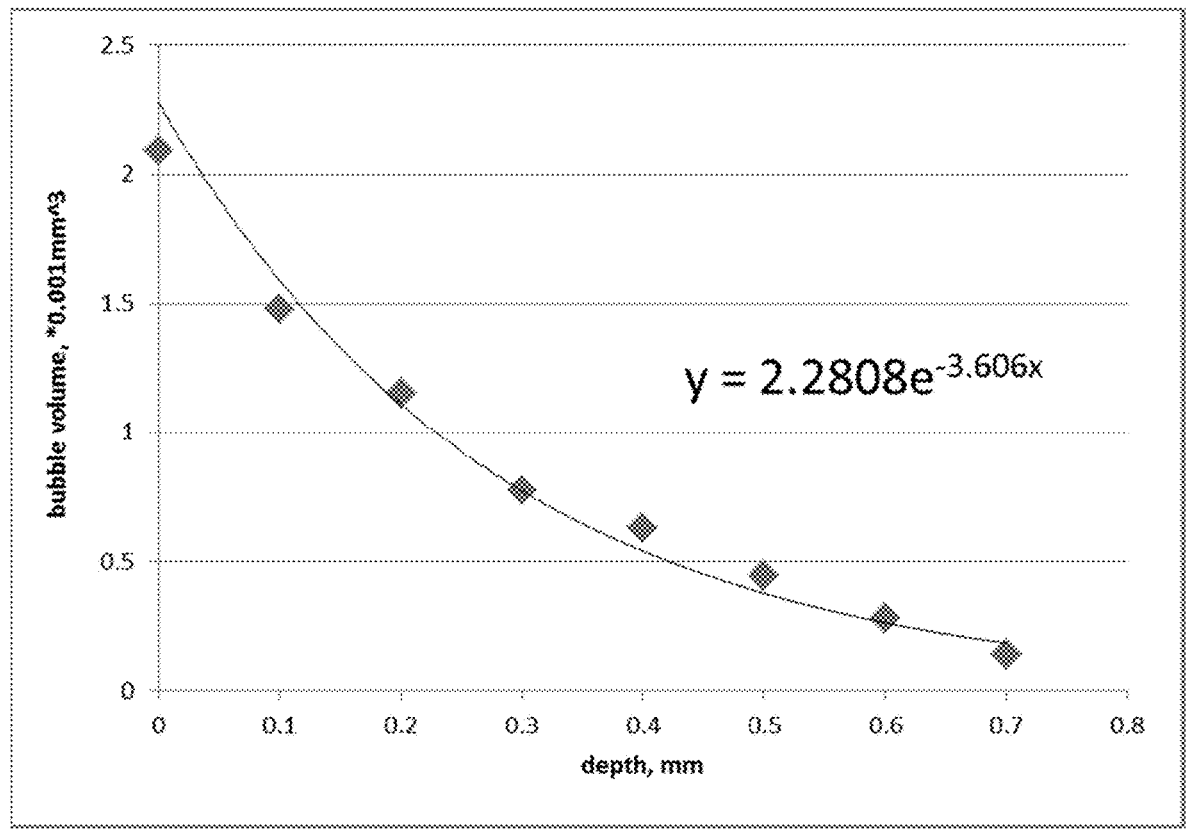
FIG. 5 is a graph illustrating bubble volume versus cut depth in a lens cut, in accordance with many embodiments.

FIG. 5 is a graph illustrating bubble volume versus cut depth in a lens cut, in accordance with many embodiments. A bubble volume measurement represents an intensity of local tissue treatment and it is assumed that the energy in the focal spot of a laser pulse is transferred into the mechanical energy of the bubble. FIG. 5 illustrates that along a depth of the lens, a bubble volume for a given energy level of a laser pulse decays exponentially. For a lens cut performed at a single energy, the consistency of the cut will vary continuously since the bubble volume decays exponentially. Therefore, maintaining a single energy level throughout a depth of the cut provides poor cut quality. The index of the exponent is a function of the initial energy. The bubble volume V may be expressed by the following equation 1:

$$V = V_0 \exp\left[-\frac{xE_{th}}{x_{0(E-E_{th})}}\right] \quad \text{(eq. 1)}$$

Where $V_0$ is a bubble coefficient, $E_{th}$ is bubble threshold energy, E is the laser pulse energy, $x_0$ is penetration depth at $2E_{th}$, and x is the depth of the cut.

Accordingly, to provide a consistent and uniform laser fragmentation cut along a depth of a lens, a bubble volume should maintain the same size throughout an entire depth of the cut. Setting the bubble volume V as a constant value const, equation 1 may be reduced to equation 2:

$$\frac{xE_{th}}{x_{0(E-E_{th})}} = const \quad \text{(eq. 2)}$$

Solving for E provides for equation 3:

$$E = E_{th} + \left[1 + \frac{x}{const\ x_0}\right] \quad \text{(eq. 3)}$$

Typically, the energy threshold $E_{th}$ and depth x are known values. The energy E may be preferably selected to be within a range of 2-10 times the threshold energy $E_{th}$ to achieve a bubble volume that provides a high quality lens cut. In a non-limiting example, if E is set to 5 $E_{th}$, then const in equation 2 can be solved for. Then substituting the solved const into equation 3 results in equation 4:

$$E = E_{th}\left[1 + \frac{4x}{x_0}\right] \quad \text{(eq. 4)}$$

Equation 4 shows that the energy E of the beam increases linearly with increasing depth to maintain a uniform bubble volume. Conversely, for a lens fragmentation that begins at a bottom of lens, the energy E should decrease linearly as the cut depth decreases to maintain a uniform bubble volume and achieve a high quality cut.

Figure 6:
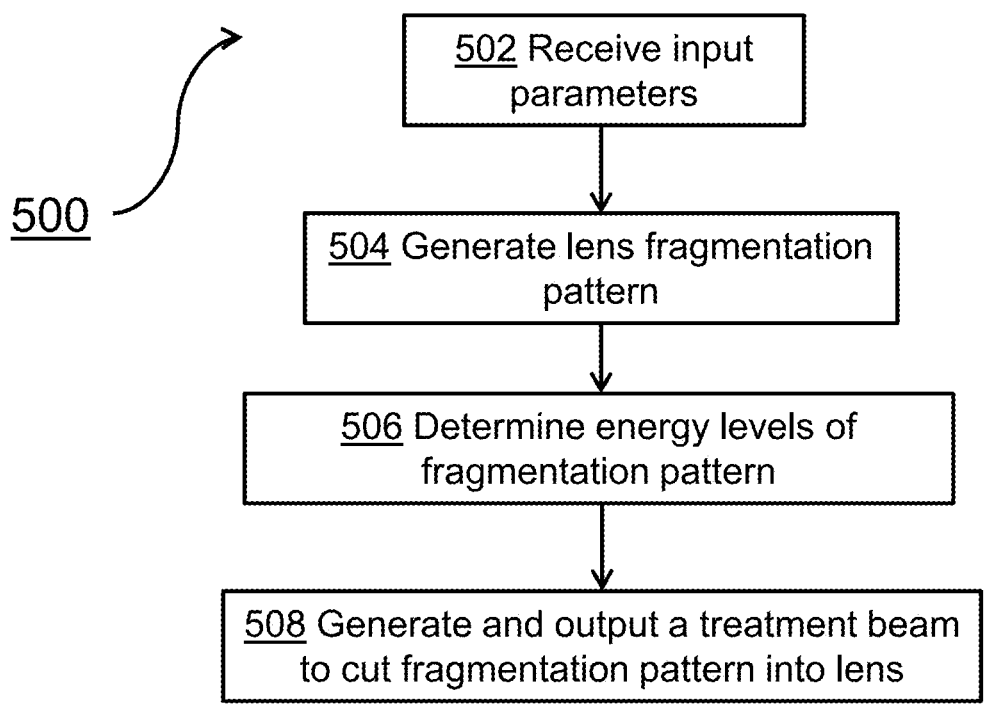
FIG. 6 shows a flowchart of a fragmentation pattern method of a lens, in accordance with many embodiments.

FIG. 6 shows a flowchart of a fragmentation pattern method 500 of a lens, in accordance with many embodiments. In the following non-limiting example, a laser beam trajectory is for lens fragmentation in cataract surgery. A laser cataract surgery system 10 is provided and includes a sub-nanosecond laser assembly 12 generating a treatment beam 28 that includes a plurality of laser beam pulses. The sub-nanosecond laser assembly 12 is, for example, a picosecond laser outputting a 150 picosecond treatment beam. The method 500 comprises the following main steps.

In step 502, the lens fragmentation process begins with reception of a plurality of input parameters. The trajectory may be computed based on fragmentation parameters including grid shape, depth, diameter, limited diameter (mm), segmentation/soft grid spacing (μm), diagnostic lens thickness (mm), spot spacing (μm), depth spacing (μm), number of cross replicates, lens anterior safe distance (μm), iris safe distance (μm), iris angle NA (deg), lens posterior safe distance (μmm), pulse energy (μJ), average power (mW), and the like.

Selection of diagnostic thickness allows the user to input a previously measured lens thickness. The diameter parameter may be maximized to the diameter of the lens segmentation or limited so as to constrain the diameter of the lens segmentation. The grid shape parameter allows selection of quadrant, sextant, and octant cuts, for example. The grid spacing parameter defines the density of the grid. The segmentation/soft grid spacing parameter defines the separation of the grid from the center of the fragmentation pattern (e.g., the middle cross). The spot spacing parameter defines the distance between laser burn spots. Lens fragmentation is performed from the posterior to anterior of the lens. Therefore, the pulse energy is selected for the bottom of the cut. The pulse energy may preferably be selected to be a value between two to ten times the threshold energy in order to provide a cut without bridging or cracking. For example, the sub-nanosecond laser source may preferably generate the treatment beam with an energy five times the energy threshold of the tissue.

In step 504, the processor determines a lens cut fragmentation pattern that defines the laser trajectory of the lens segmentation treatment. The laser trajectory includes a set of positions and corresponding energies and is based on the received input parameters.

In step 506, the set of energy settings corresponding to the trajectory positions are determined by the processor. As discussed above, the energy of the treatment beam is adjusted to match a depth of the cut according to the above equations. Specifically, the energy increases linearly with increasing depth of the cut. The energies of the treatment beam are determined as a linear function of a depth of the lens cut pattern. Since the cut begins from a bottom of the lens, the energy of the treatment beam decreases as a function of the depth of the lens linearly from the posterior to the anterior of the lens. By scaling the treatment beam energy to a depth of the lens, a consistent bubble volume is maintained to ensure a high quality cut. Scattering coefficients at each depth may be extracted from OCT, confocal scanning or video images as described above. In step 508, the processor controls the system 10 to generate and output the treatment beam 28 according to the laser trajectory and corresponding energy settings to cut the fragmentation pattern into the lens. A treatment beam 28 is generated by the sub-nanosecond laser assembly 12 and includes a plurality of laser beam pulses. The treatment beam 28 is output according to the lens cut pattern of step 504 and energies of step 506.

For lens fragmentation, the three dimensional application of laser energy can be applied across the lens in a number of fragmentation patterns as described herein. One method involves producing pattern scans consecutively at different depths with a step approximately equal to the axial length of the rupture zone of the incident laser beam. The pattern scans at each depth correspond to different portion of the lens fragmentation patter. In these sequential scans, the depth of the focal point (waist) in the tissue is stepped up or down with each consecutive scan. The laser pulses are sequentially applied to the lateral pattern at different depths of tissue using, for example, axial scanning of the focusing elements or adjusting the optical power of the focusing element while, optionally, simultaneously or sequentially scanning the lateral pattern. The adverse result of laser beam scattering on bubbles, cracks and/or tissue fragments prior to reaching the focal point can be avoided by first producing the pattern/focusing on the maximal required depth in tissue and then, in later passes, focusing on more shallow tissue spaces. This "bottom up" treatment technique reduces unwanted beam attenuation in tissue above the target tissue layer, and it also helps protect tissue underneath the target tissue layer. By scattering the laser radiation transmitted beyond the focal point on gas bubbles, cracks and/or tissue fragments which were produced by the previous scans, these defects help protect the underlying retina. Similarly, when segmenting a lens, the laser can be focused on the most posterior portion of the lens and then moved more anteriorly as the procedure continues.

It should be noted that lens fragmentation patterns scanned by the pulsed the laser system need not produce lens segments that are completely separate from each other. Rather, the laser pulses and scan patterns of the laser pulsed can be selected which result in laser induced damage tissue damage between lens segment, which make it easier to separate the segments by phacoemulsification. "Lens fragmentation," as used herein encompasses both of these results.

A number of lens fragmentations patterns are known. For instance, the lens may be split into a variable number of segments, the number of segments typically, but not always, increasing with hardness. The laser beam may, for instance, may be scanned in a pattern of two crossing cut incisions, which is preferred for cataract grades 1-3 in order to split the lens into four sections, or quadrants. For cataracts of grade 3+ and higher, a scanned pattern may three crossing cut incisions to form sextants. For the hardest cataracts of grade 4-4+, a scanned pattern of four crossing cut incisions to form octants.

Figure 7A:
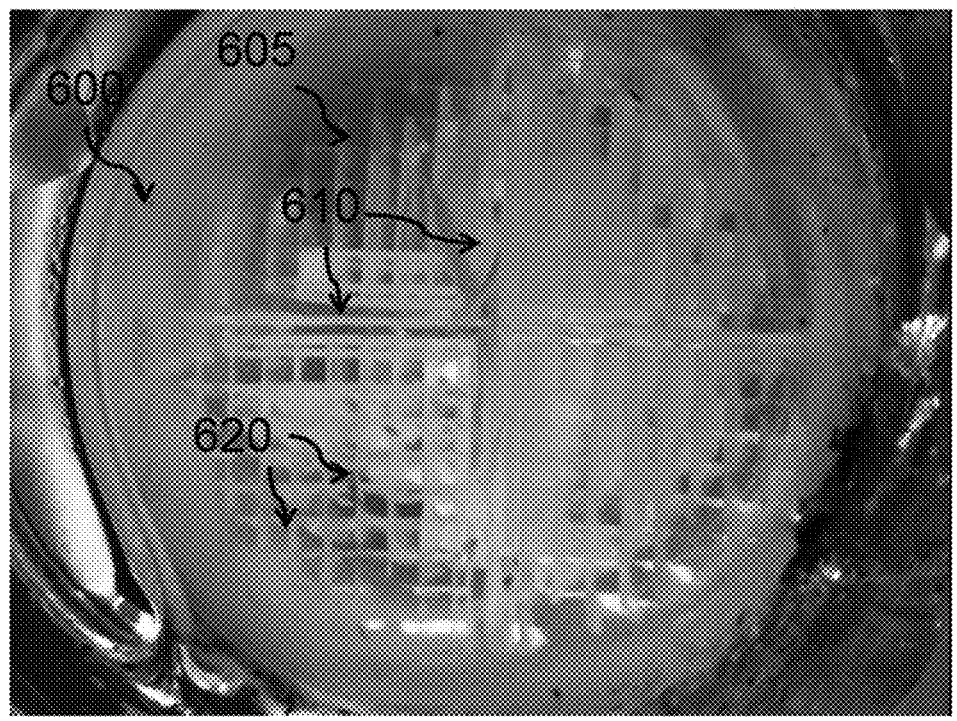
FIG. 7A is en face image of porcine lens subjected to a cataract lens fragmentation pattern by a treatment beam of a laser surgical system and showing the lateral pattern of the lens fragmentation.

FIG. 7A is en face image of porcine lens 600 subjected to a cataract lens fragmentation pattern by a treatment beam of a laser surgical system and showing the lateral pattern of the lens fragmentation. FIG. 7A depicts lens segmentation into quadrants 605 by creating planar crossed cut incisions 610 in the lens 600, together with softening cuts 620 within each quadrant to better facilitate removal of the lens by phacoemulsification. This technique combines segmenting cuts 610 that are, in many embodiments, larger (i.e. deeper, longer and/or generated with greater pulse energy), with softening cuts 620 that are, in many embodiments, smaller (shallower, shorter and/or generated with less pulse energy). The distance between the splitting and softening cuts are selected based on the hardness of the lens. The central plane cuts 610 allow the lens splitting forces to penetrate all the way out to the lens cortex, better assuring the reliable propagation of cracks along cuts 610.

Figure 7B:
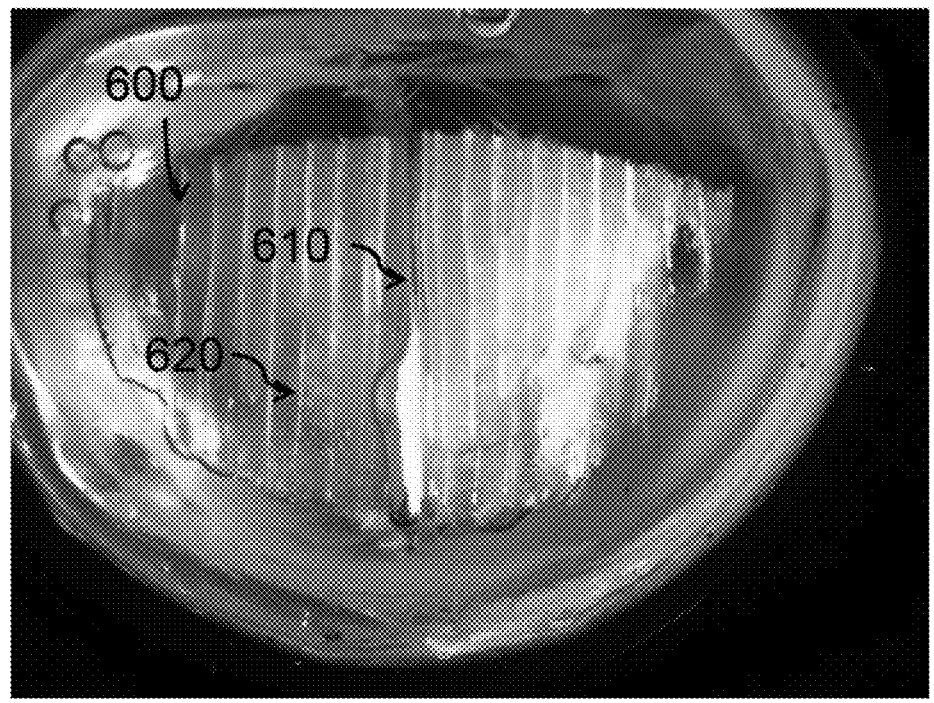
FIG. 7B is a cross sectional image of a porcine lens of FIG. 7A showing the depth wise penetration of the lens fragmentation pattern.

FIG. 7B is a cross sectional image of a porcine lens of FIG. 7A showing the depth wise penetration of the lens fragmentation pattern.

Figure 8:
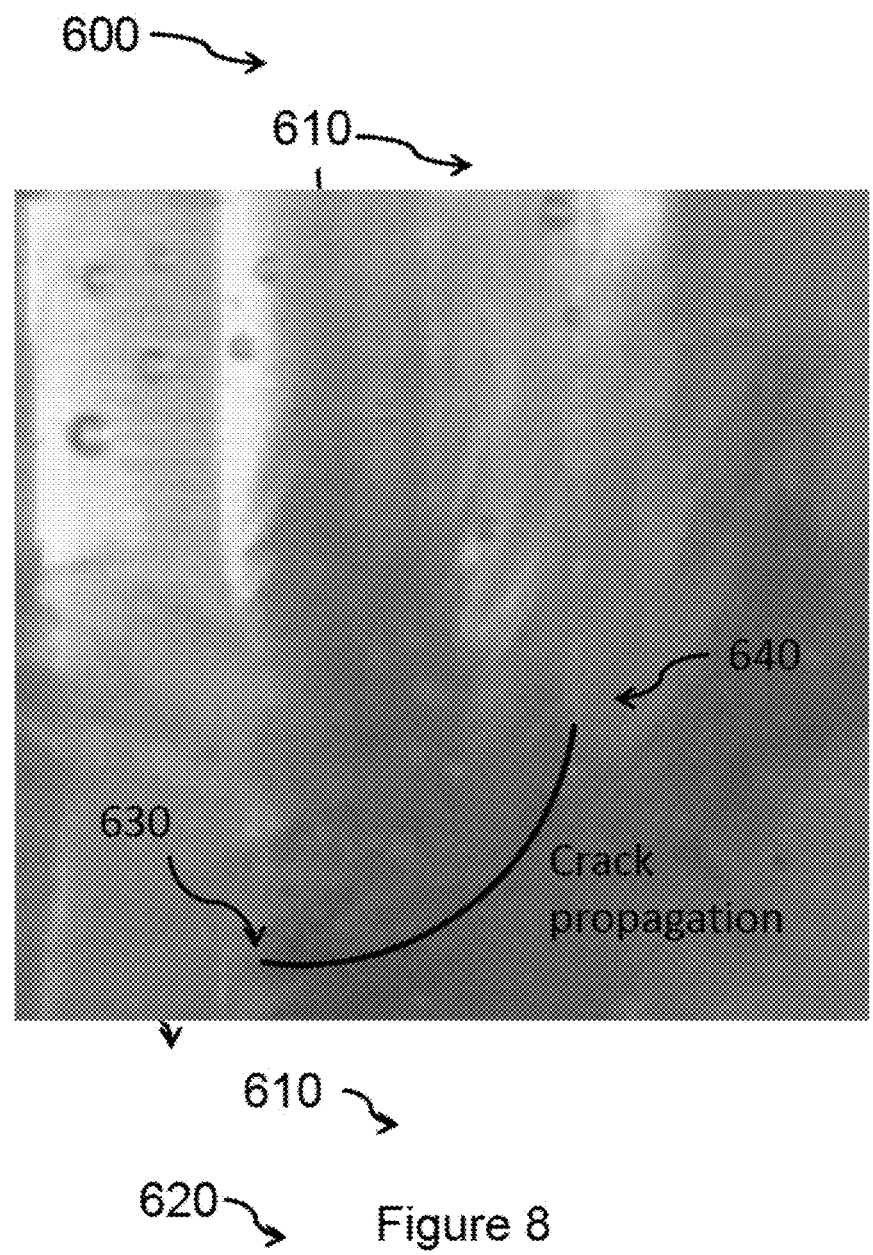
FIG. 8 is an expanded view the depth wise penetration of the lens fragmentation pattern showing a lamellar separation of lens layers induced by scanning the treatment beam in the posterior portion of the lens.

As noted above, the "bottom up" treatment technique is intended to reduce unwanted beam attenuation in tissue anterior to the target tissue layer being scanned and also to help protect tissue posterior to the target tissue layer. However, the cross-sectional structure of the crystalline lens taken along the optical axis comprises numerous layers of concentric ellipsoids. Applicants have noted that laser cuts along the optical axis in the posterior region of the lens can create lamellar separation between the concentric ellipsoids of the lens. FIG. 8 is an expanded view the depth wise penetration of the lens fragmentation pattern showing a lamellar separation of lens layers induced by scanning the treatment beam in the posterior portion of the lens. In the posterior portion of the lens, as shown in FIG. 8, these lamellar separations propagate in a lateral direction from a central portion 630 of the lens at or near the optical axis to the lens periphery 640 and in a depth wise direction from the posterior to the anterior. For purposes of the lens fragmentation patterns discussed herein, the posterior portion of the lens is that region of the lens in which the concentric lamellar ellipsoids propagate from the posterior to the anterior in a depth wise direction.

These lamellar separations (or "fractures"), generated in the posterior portion of the lens during a "bottom up" scan, attenuate, scatter or otherwise interfere with anterior off-axis pulses in subsequently scanned anterior layers (after step ups in the bottom up scan pattern), which may explain why deepest incisions in a depth wise direction in lens fragmentation scanning patterns are often at the central portion of the lens.

Figure 9:
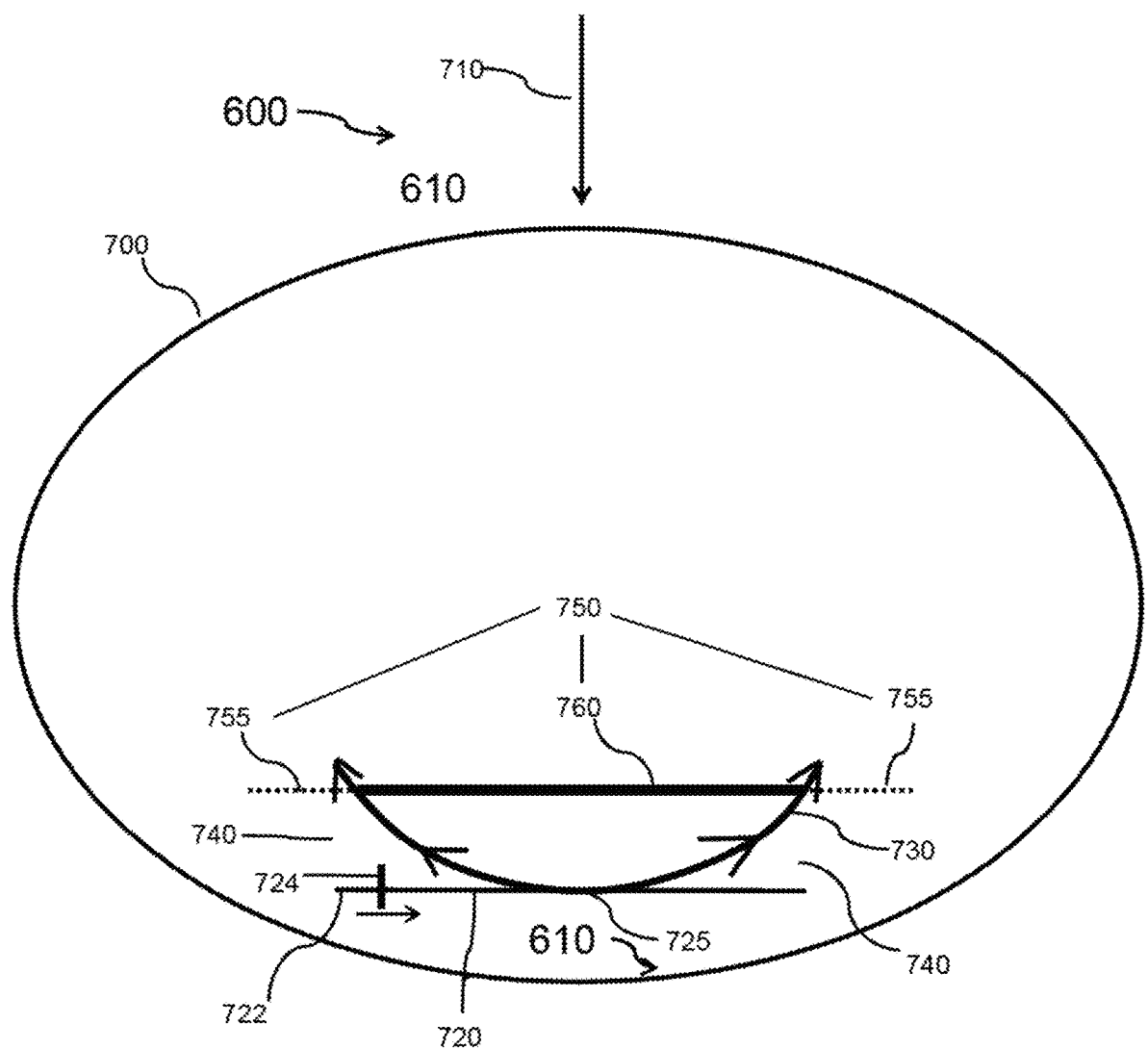
FIG. 9 is a graphical illustration of the lamellar separation caused by laser scans along the optical axis in the posterior portion of the lens.

FIG. 9 is a graphical illustration of several aspects of the present invention. FIG. 9 shows a cross-section 700 of the eye in which a first incision (or "scan") pattern 720 at a first depth within the eye 700 and a second incision pattern 750 located anterior to the first incision pattern 720 are disposed in the posterior portion of the eye. The first incision pattern 720 includes a central portion 725 at or near the optical axis of the eye and a peripheral portion 722 laterally spaced from the central portion 725. In the conventional bottom up scan, the laser proceeds in a stepwise manner from the deepest scan toward the anterior, and as such the first incision pattern 720 would be scanned first and then the second incision pattern 750 would be scanned. Note that in FIG. 9, laser scan patterns 720, 750 need not adjacent scans and intervening laser scan layers (not shown) may be between laser scan patterns 720, 750.

As illustrated in FIG. 9, laser pulses directed along optical axis 710 at the central portion 725 of first scan pattern 720 can induce a lamellar separation 730 propagating in a direction anterior and laterally from the central portion 725. The lamellar separation 730 has a property of attenuating or otherwise interfering with anterior off-axis laser pulses whose focal point is directed within region 740. As such, incisions created by scanning of the focal point within regions 740 may be of lesser quality, incomplete, or otherwise unsatisfactory. Regions 740 may be referred to as "fragmentation gaps." It has been experimentally determined that scanning within about 250 μm from the center of the lens can cause lamellar separation and resulting fragmentation gaps.

In order to reduce the occurrence and/or of fragmentation gaps 740, the laser is preferably controlled so as to directed laser pulses along the first scan pattern 720 beginning at a periphery of the lens and progressing toward the center of the lens. Specifically, as shown in FIG. 9, laser pulses 724 should be directed along the first incision pattern 720 in a direction from a peripheral portion 722 of the first incision pattern 720 to a central portion 725 of the first incision pattern. Without being limited to theory, laser pulses 24 of the incident laser beam have a waist length in the depth direction that produces rupture zone having an axial length that modifies tissues in the axial, or depth wise direction. This axial rupture zone of laser pulses 24 may serve to eliminate, block or otherwise limit the anterior and lateral propagation of lamellar layers, thus limiting the occurrence or extent of fragmentations zones 740.

Alternatively, if the first incision pattern 720 is scanned in a direction from the central portion 725 to the peripheral portion 722 so as to cause a lamellar separation 730, the anterior second incision pattern 750 may comprises an attenuated region 755 of scan 750 within a fragmentation zone 740 and a non-attenuated region 760 that is not subject to interference. Incisions formed by laser pulses scanned in the attenuated region 755 may be inadequate pulse energy if the same laser pulse energy is used to scan both the attenuated region 755 and the non-attenuated region 760.

As such, in many embodiments, higher laser pulse energies may be used to scan the peripheral portion of the second incision pattern 750 than the central portion in order to ensure effective cuts in the attenuated regions 755 of the incision planes The processor system may comprise tangible medium embodying instructions of a computer program to perform one or more of the method steps as described herein.

As used herein, like characters such as reference numerals and letters describe like elements. As used herein, Photodisruption generally refers to visible damage in tissue caused by a pulsed laser beam. An energy threshold for photodisruption generally means an energy level of laser beam pulses that cause the first visible damage in tissue.

As used herein, the terms anterior and posterior refer to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A laser surgical system for making incisions in a lens of a patient's eye during a cataract surgical procedure, the system comprising:
   a laser system comprising a scanning assembly and a laser operable to generate a laser beam configured to incise the lens of the eye; and
   a control system operably coupled to the laser system and configured to:
   determine a lens fragmentation scanning pattern for scanning a focal zone of the laser beam in a cutting region in a posterior portion of the lens of the eye, the cutting region being at least partially defined by an anterior cutting boundary, a posterior cutting boundary and a lateral cutting boundary of the lens, the cutting region including the optical axis of the eye and a peripheral portion of the lens spaced laterally from the optical axis;
   operate the laser and the scanning assembly to scan the focal zone of the laser beam at a first focal point located at a first depth in the lens of the eye and to scan the beam on the eye while focused at the first depth so as to create a first incision pattern in the lens corresponding to a first portion of the lens fragmentation pattern, and
   operate the laser and scanning assembly to scan the focal zone of the laser beam at a second focal point located at a second depth in the lens of the eye anterior to the first depth, and to scan the beam on the eye while focused at the second depth so as to create a second incision pattern in the lens corresponding to a second portion of the lens fragmentation pattern within the cutting region at the second depth, wherein an energy of the laser pulses scanning the second incision pattern is higher when the second focal point is scanned in the peripheral portion than when the second focal point is scanned in a central portion near the optical axis.

2. The system of claim 1, further comprising:
   an imaging device configured to acquire point by point image data from locations distributed throughout a volume of the lens of the patient and construct one or more images of the patient's eye tissues from the image data, wherein the one or more images comprise an image of at least a portion of the lens; and
   wherein the control system is further configured to:
   operate the imaging device to generate image data for patient's lens;
   process the image data to identify a location for each of one or more targets in the lens, the one or more targets within the cutting region.

3. The system of claim 1, wherein the lens fragmentation pattern comprises either two crossing cut incisions, three crossing cut incisions or four crossing cut incisions.

4. The system of claim 3, wherein the lens fragmentation pattern comprises two and only two crossing cut incisions, thereby producing four quadrants.

5. The system of claim 4, wherein the lens fragmentation pattern further comprises softening cuts in each quadrant.

6. A laser surgical system for making incisions in a lens of a patient's eye during a cataract surgical procedure, the system comprising:
a laser system comprising a scanning assembly and a laser operable to generate a laser beam configured to incise the lens of the eye; and
a control system operably coupled to the laser system and configured to:
determine a lens fragmentation scanning pattern for scanning a focal zone of the laser beam in a cutting region in a posterior portion of the lens of the eye, the cutting region being at least partially defined by an anterior cutting boundary, a posterior cutting boundary and a lateral cutting boundary of the lens, the cutting region including the optical axis of the eye and a peripheral portion of the lens spaced laterally from the optical axis;
operate the laser and the scanning assembly to scan the focal zone of the laser beam at a first focal point located at a first depth in the lens of the eye and to scan the beam on the eye while focused at the first depth in a lateral direction from a peripheral portion of the lens toward the optical axis of the eye so as to create a first incision pattern in the lens corresponding to first portion of the lens fragmentation pattern; and
operate the laser and scanning assembly to scan the focal zone of the laser beam at a second focal point located at a second depth in the lens of the eye anterior to the first depth, and to scan the beam on the eye while focused at the second depth so as to create a second incision pattern in the lens corresponding to a second portion of the lens fragmentation pattern within the cutting region at the second depth.

7. The system of claim 6, further comprising:
an imaging device configured to acquire point by point image data from locations distributed throughout a volume of a lens of the patient and construct one or more images of the patient's eye tissues from the image data, wherein the one or more images comprise an image of at least a portion of the lens; and
wherein the control system is further configured to:
operate the imaging device to generate image data for patient's lens;
process the image data to identify a location for each of one or more targets in the lens, the one or more targets within the cutting region.

8. The system of claim 7, wherein the lens fragmentation pattern comprises either two crossing cut incisions, three crossing cut incisions or four crossing cut incisions.

9. The system of claim 8, wherein the lens fragmentation pattern comprises two and only two crossing cut incisions, thereby producing 4 quadrants.

10. The system of claim 9, wherein the lens fragmentation patter further comprises softening cuts in each quadrant.

11. A method implemented in a laser surgical system for making incisions in a lens of a patient's eye during a cataract surgical procedure, the method comprising:
by a laser source of the laser surgical system, generating a laser beam;
by a scanning assembly of the laser surgical system, directing a focal zone of the laser beam to locations within the lens of the eye;
by a control system, determine a lens fragmentation scanning pattern for scanning a focal zone of the laser beam in a cutting region in a posterior portion of the lens of the eye, the cutting region being at least partially defined by an anterior cutting boundary, a posterior cutting boundary and a lateral cutting boundary of the lens, the cutting region including the optical axis of the eye and a peripheral portion of the lens spaced laterally from the optical axis;
by the control system, operating the laser and the scanning assembly to scan the focal zone of the laser beam at a first focal point located at a first depth in the lens of the eye and to scan the beam on the eye while focused at the first depth so as to create a first incision pattern in the lens corresponding to a first portion of the lens fragmentation pattern, and
by the control system, operating the laser and scanning assembly to scan the focal zone of the laser beam at a second focal point located at a second depth in the lens of the eye anterior to the first depth, and to scan the beam on the eye while focused at the second depth so as to create a second incision pattern in the lens corresponding to a second portion of the lens fragmentation pattern within the cutting region at the second depth, wherein an energy of the laser pulses scanning the second incision pattern is higher when the second focal point is scanned in the peripheral portion than when the second focal point is scanned in a central portion near the optical axis.

12. The method of claim 11, further comprising:
by an imaging device, acquiring point by point image data from locations distributed throughout a volume of the lens of the patient and constructing one or more images of the patient's eye tissues from the image data, wherein the one or more images comprise an image of at least a portion of the lens; and
by the control system, operate the imaging device to generate image data for patient's lens;
by the control system, process the image data to identify a location for each of one or more targets in the lens, the one or more targets within the cutting region.

13. The method of claim 11, wherein the lens fragmentation pattern comprises either two crossing cut incisions, three crossing cut incisions or four crossing cut incisions.

14. The method of claim 13, wherein the lens fragmentation pattern comprises two and only two crossing cut incisions, thereby producing four quadrants.

15. The method of claim 14, wherein the lens fragmentation pattern further comprises softening cuts in each quadrant.

* * * * *